(12) United States Patent
Kirchhofer et al.

(10) Patent No.: US 7,737,115 B2
(45) Date of Patent: Jun. 15, 2010

(54) HGF BETA CHAIN VARIANTS

(75) Inventors: Daniel K. Kirchhofer, Los Altos, CA (US); Robert A. Lazarus, Millbrae, CA (US); Christian Wiesmann, Brisbane, CA (US)

(73) Assignee: Genetech, Inc., South San Francisco, CA (US)

( * ) Notice: Subject to any disclaimer, the term of this patent is extended or adjusted under 35 U.S.C. 154(b) by 165 days.

(21) Appl. No.: 11/406,067

(22) Filed: Apr. 17, 2006

(65) Prior Publication Data

US 2006/0293235 A1 Dec. 28, 2006

Related U.S. Application Data

(60) Provisional application No. 60/671,610, filed on Apr. 15, 2005.

(51) Int. Cl.
 *A61K 38/18* (2006.01)
(52) U.S. Cl. ...................................................... 514/12
(58) Field of Classification Search ........................ None
 See application file for complete search history.

(56) References Cited

U.S. PATENT DOCUMENTS

| 4,342,566 | A |  | 8/1982 | Theofilopoulos et al. |
| 4,816,567 | A |  | 3/1989 | Cabilly et al. |
| 5,227,158 | A |  | 7/1993 | Jardieu |
| 5,316,921 | A |  | 5/1994 | Godowski et al. |
| 5,328,837 | A |  | 7/1994 | Godowski et al. |
| 5,362,716 | A |  | 11/1994 | Kmiecik et al. |
| 5,547,856 | A |  | 8/1996 | Godowski et al. |
| 5,871,959 | A |  | 2/1999 | Rong et al. |
| 5,879,910 | A | * | 3/1999 | Godowski et al. .......... 435/69.4 |
| 6,207,152 | B1 |  | 3/2001 | Schwall et al. |
| 6,214,344 | B1 |  | 4/2001 | Schwall et al. |
| 6,468,529 | B1 |  | 10/2002 | Schwall et al. |

FOREIGN PATENT DOCUMENTS

| EP | 0 567 585 B1 | 11/1993 |
| WO | WO 92/05184 | 4/1992 |
| WO | WO 92/13097 | 8/1992 |
| WO | WO 92/20792 | 11/1992 |
| WO | WO 93/15754 | 8/1993 |
| WO | WO 93/23541 | 11/1993 |
| WO | WO 93/23550 | 11/1993 |
| WO | WO 94/04679 | 3/1994 |
| WO | WO 94/06909 | 3/1994 |
| WO | WO 94/29348 | 12/1994 |
| WO | WO 95/01376 | 1/1995 |
| WO | WO 98/19696 | 5/1998 |
| WO | 2005/001486 | 1/2005 |

OTHER PUBLICATIONS

Angeloni et al., "The Soluble Sema Domain of the RON Receptor Inhibits Macrophage-stimulating Protein-induced Receptor Activation" *Journal of Biological Chemistry* 279(5):3726-3732 (Jan. 2004).
Asami et al., "Purification and Characterization of Hepatocyte Growth Factor from Injured Liver of Carbon Tetrachloride-Treated Rats" *J Biochem* (Tokyo) 109(1):8-13 (Jan. 1991).
Bellusci et al., "Creation of an Hepatocyte Growth Factor/Scatter Factor Autocrine Loop in Carcinoma Cells Induces Invasive Properties Associated with Increased Tumorigenicity" *Oncogene* 9(4):1091-1099 (Apr. 1994).
Birchmeier et al., "Met, Metastasis, Motility and More" *Nature Reviews Molecular Cell Biology* 4:915-925 (Dec. 2003).
Boerner et al., "Production of Antigen-Specific Human Monoclonal Antibodies From In Vitro-Primed Human Splenocytes" *The Journal of Immunology* 147(1):86-95 (Jul. 1991).
Boose et al., "The Single-Chain Form of Tissue-Type Plasminogen Activator Has Catalytic Activity: Studies with a Mutant Enzyme That Lacks the Cleavage Site" *Biochemistry* 28(2):635-643 (Jan. 24, 1989).
Bottaro et al., "Identification of the Hepatocyte Growth Factor Receptor as the c-met Proto-Oncogene Product" *Science* 251:802-804 (Feb. 15, 1991).
Brodeur et al., "Mouse-Human Myeloma Partners for the Production of Heterohybridomas" *Monoclonal Antibody Production Techniques and Applications*, New York:Marcel Dekker, Inc. pp. 51-63 (1987).
Broze Jr. et al., "Protein Z-Dependent Regulation of Coagulation" *Thromb. Haemost.* 86(1):8-13 (Jul. 2001).
Bruggemann et al., "Designer Mice: The Production of Human Antibody Repertoires in Transgenic Animals" *Year in Immunology* 7:33-40 (1993).
Carter et al., "Humanization of an Anti-p185[HER2] Antibody For Human Cancer Therapy" *Proc. Natl. Acad. Sci. USA* 89(10):4285-4289 (May 1992).
Chamow et al., "A Humanized, Bispecific Immunoadhesin-Antibody That Retargets CD3[+] Effectors to Kill HIV-1-Infected Cells" *Journal of Immunology* 153(9):4268-4280 (Nov. 1, 1994).
Chan et al., "Identification of a Competitive HGF Antagonist Encoded by an Alternative Transcript" *Science* 254(5036):1382-1385 (Nov. 29, 1991).
Chan et al., "Isoforms of Human HGF and Their Biological Activities" *Hepatocyte Growth Factor-Scatter Factor (HGF-SF) and the C-Met Receptor*, I.D. Goldberg and E.M. Rosen eds., Basel: Birkhauser Verlag pp. 67-79 (1993).
Chirgadze et al., "Insights into the structure of hepatocyte growth factor/scatter factor (HGF/SF) and implication for receptor activation" *FEBS Letters* 430:126-129 (1998).
Chothia and Lesk, "Canonical Structures for the Hypervariable Regions of Immunoglobulins" *J Mol Biol.* 196(4):901-917 (Aug. 20, 1987).

(Continued)

Primary Examiner—Marianne P Allen
(74) Attorney, Agent, or Firm—Cara M. Coburn

(57) ABSTRACT

The invention provides HGF/Met modulators comprising HGF having mutations in regions that affect HGF function, and antagonists that target said regions. The invention further provides methods of identifying, making and using these modulators.

17 Claims, 5 Drawing Sheets

OTHER PUBLICATIONS

Chothia et al., "Domain Association in Immunoglobulin Molecules. The Packing of Variable Domains" *Journal of Molecular Biology* 186(3):651-663 (Dec. 5, 1985).

Cohen, G., "ALIGN: a program to superimpose protein coordinates, accounting for insertions and deletions" *J Appl. Crystallog.* 30:1160-1161 (1997).

Cole et al., "The EBV-Hybridoma Technique and Its Application to Human Lung Cancer" *Monoclonal Antibodies and Cancer Therapy*, New York:Alan R. Liss, Inc. pp. 77-96 (1985).

Collaborative Computational Project, No. 4, "The CCP4 suite: programs for protein crystallography." *Acta Crystallogr D Biol Crystallogr.* 50(Pt 5):760-763 (Sep. 1, 1994).

Comoglio et al., "The Met/HGF-SF Receptor" *Positive Growth Control* (Abstract Only) 192:H215.

Comoglio, "Structure, Biosynthesis and Biochemical Properties of the HGF Receptor in Normal and Malignant Cells" *Hepatocyte Growth Factor-Scatter Factor (HGF/SF) and the C-Met Receptor*, I.D. Goldberg and E.M. Rosen eds., Basel:Birkhauser Verlag pp. 131-165 (1993).

Comoglio, "The HGF Receptor and Its Ligand: Structure, Signal Transduction and Biology" *Cell Biology International* (abstract only) 18(5):375 (1994).

Cooper et al., "Amplification and Overexpression of the MET Gene in Spontaneously Transformed NIH3T3 Mouse Fibroblasts" *EMBO Journal* 5(10):2623-2628 (Oct. 1986).

Cooper et al., "Characterization of Human Transforming Genes from Chemically Transformed, Teratocarcinoma, and Pancreatic Carcinoma Cell Lines" *Cancer Research* 44 (1):1-10 (Jan. 1984).

Cooper et al., "Molecular cloning of a new transforming gene from a chemically transformed human cell line" *Nature* 311(5981):29-33 (Sep. 6, 1984).

Crepaldi et al., "Targeting of the SF/HGF Receptor to the Basolateral Domain of Polarized Epithelial Cells" *J Cell Biol.* (J Cell Biol. Apr. 1994;125(2):313-20) 125(2):313-320 (Apr. 1994).

Danilkovitch et al., "Interaction of macrophage-stimulating protein with its receptor. Residues critical for beta chain binding and evidence for independent alpha chain binding" *J Biol Chem.* 274(42):29937-29943 (Oct. 15, 1999).

Danilkovitch-Miagkova & Zbar, "Dysregulation of Met receptor tyrosine kinase activity in invasive tumors" *The Journal of Clinical Investigation* 109(7):863-867 (Apr. 2002).

Date et al., "HGF/NK4 is a specific antagonist for pleiotrophic actions of hepatocyte growth factor" *FEBS Letters* 420(1):1-6 (Dec. 22, 1997).

David and Reisfeld, "Protein Iodination with Solid State Lactoperoxidase" *Biochemistry* 13(5):1014-1021 (Feb. 26, 1974).

de Sauvage et al., "Stimulation of Megakaryocytopoiesis and Thrombopoiesis by the c-Mpl Ligand" *Nature*369(6481):533-538 (Jun. 16, 1994).

Defrances et al., "The Presence of Hepatocyte Growth Factor in the Developing Rat" *Development* 116(2):387-395 (Oct. 1992).

Dennis et al., "Peptide Exosite Inhibitors of Factor VIIa as Anticoagulants" *Nature* 404(6777):465-470 (Mar. 30, 2000).

Derksen et al., "Cell surface proteoglycan syndecan-1 mediates hepatocyte growth factor binding and promotes Met signaling in multiple myeloma" *Blood* 99(4):1405-1410 (2002).

Di Cera et al., "The Na+ binding site of Thrombin" *Journal of Biological Chemistry* 270(38):22089-22092.

Di Renzo et al., "Overexpression of the c-MET/HGF Receptor Gene in Human Thyroid Carcinomas" *Oncogene* 7(12):2549-2553 (Dec. 1992).

Di Renzo et al., "Selective Expression of the Met/HGF Receptor in Human Central Nervous System Microglia" *Oncogene* 8:219-222 (1993).

Dickinson et al., "Identification of surface residues mediating tissue factor binding and catalytic function of the serine protease factor VIIa" *Proc. Natl. Acad. Sci USA* 93(25):14379-14384 (Dec. 10, 1996).

Donate et al., "Molecular evolution and domain structure of plasminogen-related growth factors (HGF/SF and HGFI/MSP)" *Protein Sci.* 3:2378-2394 (1994).

Drain et al., "Haptoglobin-related Protein Mediates Tyrpanosome Lytic Factor Binding to Trypanosomes" *Journal of Biological Chemistry* (J. Biol. Chem., 32,) 276(32):30254-30260 (Aug. 10, 2001).

Fan et al., "Blockade of Epidermal Growth Factor Receptor Function by Bivalent and Monovalent Fragments of 225 Anti-Epidermal Growth Factor Receptor Monoclonal Antibodies" *Cancer Research* 53(18):4322-4328 (Sep. 15, 1993).

Gherardi et al., "Functional map and domain structure of MET, the product of the c-met protooncogene and receptor for hepatocyte growth factor/scatter factor" *Proc. Natl. Acad. Sci. USA* 100(21):12039-12044 (Oct. 14, 2003).

Giordano et al., "Transfer of Motogenic and Invasive Response to Scatter Factor/Hepatocyte Growth Factor by Transfection of Human met Protooncogene" *Proc. Natl. Acad. Sci. USA* 90(2):649-653 (Jan. 15, 1993).

Giordano et al., "Tyrosine Kinase Receptor Indistinguishable from the C-Met Protein" *Nature* 339(6220):155-156 (May 11, 1989).

Goding, "Production of Monoclonal Antibodies" *Monoclonal Antibodies: Principles and Practice*, Academic Press, pp. 59-103 (1986).

Gohda et al., "Purification and Partial Characterization of Hepatocyte Growth Factor from Plasma of a Patient with Fulminant Hepatic Failure" *J. Clin. Invest.* 81(2):414-419 (Feb. 1988).

Gorman, C., "High Efficiency Gene Transfer Into Mammalian Cells" *DNA Cloning: A Practical Approach*, Glover, D.M., ed, Washington D.C.:IRL Press vol. 2:143-190 (1985).

Han et al., "Characterization of the DNF15S2 Locus on Human Chromosome 3: Identification of a Gene Coding for Four Kringle Domains with Homology to Hepatocyte Growth Factor" *Biochemistry* 30(40):9768-9780 (Oct. 8, 1991).

*Handbook of Monoclonal Antibodies*, Ferrone et al. eds., Park Ridge, NJ:Noyes Publications, pp. 293-359 and Chapter 22 (1985).

Harris et al., "Therapeutic Antibodies—The Coming of Age" *TIBTECH* 11(2):42-44 (Feb. 1993).

Hartmann et al., "A Functional Domain in the Heavy Chain of Scatter Factor/Hepatocyte Growth Factor Binds the c-Met Receptor and Induces Cell Dissociation but Not Mitogenesis" *Proc. Natl. Acad. Sci. USA* 89(23):11574-11578 (Dec. 1, 1992).

Hartmann et al., "Engineered mutants of HGF/SF with reduced binding to heparan sulphate proteoglycans, decreased clearance and enhanced activity in vivo" *Curr. Biol.* 8(3):125-134 (Jan. 29, 1998).

Hedstrom, L., "Serine Protease Mechanism and Specificty" *Chem. Rev.* 102(12):4501-4523 (Dec. 2002).

Hoogenboom and Winter, "By-passing immunisation. Human antibodies from synthetic repertoires of germline VH gene segments rearranged in vitro" *J. Mol. Biol.* 227(2):381-388 (Sep. 20, 1992).

Huber and Bode, "Structural Basis of the Activation and Action of Trypsin" *Accounts of Chemical Research* 11:114-122 (1978).

Hunter et al., "Preparation of Iodine-131 Labelled Human Growth Hormone of High Specific Activity" *Nature* 194(4827):495-496 (May 5, 1962).

Igawa et al., "Hepatocyte Growth Factor is a Potent Mitogen for Cultured Rabbit Renal Tubular Epithelial Cells" *Biochem. & Biophys. Res. Comm.* 174(2):831-838 (Jan. 31, 1991).

Iyer et al., "Structure, Tissue-Specific Expression, and Transforming Activity of the Mouse met Protooncogene" *Cell Growth Differ.* 1(2):87-95 (Feb. 1990).

J. E. Illingworth, "The Relationship Between Ultraviolet Radiation and Epithelial Cancer" *Medical Hypotheses* 19(2):155-159 (Feb. 1986).

Jakobovits et al., "Analysis of Homozygous Mutant Chimeric Mice: Deletion of the Immunoglobulin Heavy-Chain Joining Region Blocks B-cell Development and Antibody Production" *Proc. Natl. Acad. Sci. USA* 90(6):2551-2555 (Mar. 15, 1993).

Jakobovits et al., "Germ-line Transmission and Expression of a Human-Derived Yeast Artificial Chromosome" *Nature* 362(6417):255-258 (Mar. 18, 1993).

Jones et al., "Replacing the Complementarity-Determining Regions in a Human Antibody with Those From a Mouse" *Nature* 321(6069):522-525 (May 29, 1986).

Kabat et al., "Sequences of Proteins of Immunological Interest", Bethesda, MD:National Institute of Health (1983).

Kirchhofer et al., "Hepsin activates pro-hepatocyte growth factor and is inhibited by hepatocyte growth factor activator inhibitor-1B (HAI-1B) and HAI-2" *FEBS Letters* 579(9):1945-1950 (Mar. 28, 2005).

Kohler and Milstein, "Continuous Cultures of Fused Cells Secreting Antibody of Predefined Specificity" *Nature* 256(5517):495-497 (Aug. 7, 1975).

Kozbor et al., "A Human Hybrid Myeloma for Production of Human Monoclonal Antibodies" *J. Immunol.* 133(6):3001-3005 (Dec. 1, 1984).

Kunkel, T., "Rapid and Efficient Site-Specific Mutagenesis Without Phenotypic Selection" *Proc. Natl. Acad. Sci.* 82(2):488-492 (Jan. 1985).

Kurosky et al., "Covalent structure of human haptoglobin: A serine protease homolog" *Proc. Natl. Acad. Sci. USA* 77(6):3388-3392 (Jun. 1980).

Lijnen et al., "Plasminogen Activation with Single-chain Urokinase-type Plasmingoen Activator (scu-PA)" *J Biol Chem.* 265(9):5232-5236 (Mar. 25, 1990).

Lin et al., "Molecular cloning of cDNA for matriptase, a matrix-degrading serine protease with trypsin-like activity" *J Biol Chem.* 274(26):18231-18236 (Jun. 25, 1999).

Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Administration" *Hepatology* 13(4):743-750 (Apr. 1991).

Lokker et al., "Generation and Characterization of a Competitive Antagonist of Human Hepatocyte Growth Factor, HGF/NK1" *Journal of Biological Chemistry* 268(23):17145-17150 (Aug. 15, 1993).

Lokker et al., "Mutational analysis and molecular modeling of the N-terminal kringle-containing domain of hepatocyte growth factor identifies amino acid side chains important for interaction with the c-Met receptor" *Protein Eng.* 7(7):895-903 (Jul. 1994).

Ma Patrick C. et al., "c-Met: Structure, functions and potential for therapeutic inhibition" *Cancer and Metastasis Reviews* 22(4):309-325 (Dec. 2003).

Malkowski et al., "The co-crystal structure of unliganded bovine α-thrombin and prethrombin-2: Movement of the Tyr-Pro-Pro-Trp segment and active site residues upon ligand binding" *Protein Sci.* 6(7):1438-1448 (Jul. 1997).

Mark et al., "Expression and Characterization of Hepatocyte Growth Factor Receptor-IgG Fusion Proteins" *The Journal of Biological Chemistry* 267(36):26166-26171 (Dec. 25, 1992).

Marks et al., "By-Passing Immunization: Human Antibodies From V-gene Libraries Displayed On Phage" *J. Mol. Biol.* 222(3):581-597 (Dec. 5, 1991).

Matsumoto et al., "Cooperative Interaction between α- and β- Chains of Heptocyte Growth Factor on c-Met Receptor Confers Ligand-induced Receptor Tyrosine Phosphorylation and Multiple Biological Responses" *Journal of Biological Chemistry* 273(36):22913-22920 (Sep. 4, 1998).

Matsumoto et al., "Deletion of Kringle Domains or the N-Terminal Hairpin Structure in Hepatocyte Growth Factor Results in Marked Decreases in Related Biological Activities" *Biochem. & Biophys. Res. Comm.* 181(2):691-699 (Dec. 16, 1991).

Matsumoto et al., "Hepatocyte Growth Factor is a Potent Stimulator of Human Melanocyte DNA Synthesis and Growth" *Biochem. & Biophys. Res. Comm.* 176(1):45-51 (Apr. 15, 1991).

Maulik et al., "Role of the hepatocyte growth factor receptor, c-Met, in oncogenesis and potential for therapeutic inhibition" *Cytokine & Growth Factor Reviews* 13(1):41-59 (Feb. 2002).

Michalopoulos et al., "Control of Hepatocyte Replication by Two Serum Factors" *Cancer Research* 44(10):4414-4419 (Oct. 1984).

Miller & Leonard, "Mode of receptor binding and activation by plasminogen-related growth factors" *FEBS Letters* 429(1):1-3 (Jun. 5, 1998).

Miyazawa et al., "An Alternatively Processed mRNA Generated from Human Hepatocyte Growth Factor Gene" *European Journal of Biochemistry* 197(1):15-22 (Apr. 10, 1991).

Miyazawa et al., "Molecular cloning and sequence analysis of cDNA for human hepatocyte growth factor" *Biochem. & Biophys. Res. Comm.* 163(2):967-973 (Sep. 15, 1989).

Miyazawa et al., "Molecular Cloning and Sequence Analysis of the cDNA for a Human Serine Protease Responsible for Activation of Hepatocyte Growth Factor" *Journal of Biological Chemistry* 268(14):10024-10028 (May 15, 1993).

Montesano et al., "Identification of a Fibroblast-Derived Epithelial Morphogen as Hepatocyte Growth Factor" *Cell* 67:901-908 (Nov. 29, 1991).

Morrison et al., "Chimeric Human Antibody Molecules: Mouse Antigen-Binding Region Domains with Human Constant Region Domains" *Proc. Natl. Acad. Sci. USA* 81(21):6851-6855 (Nov. 1984).

Munson and Rodbard, "Ligand: A Versatile Computerized Approach for Characterization of Ligand-Binding Systems" *Analytical Biochemistry* 107(1):220-239 (Sep. 1, 1980).

Naka et al., "Activation of Hepatocyte Growth Factor by Proteolytic Conversion of a Single Chain Form to a Heterodimer" *The Journal of Biological Chemistry* 267(28):20114-20119 (Oct. 5, 1992).

Nakamura et al., "Molecular Cloning and Expression of Human Hepatocyte Growth Factor" *Nature* 342:440-443 (Nov. 23, 1989).

Nakamura et al., "Partial Purification and Characterization of Hepatocyte Growth Factor from Serum of Hepatectomized Rats" *Biochem. & Biophys. Res. Comm.* 122:1450-1459 (Aug. 16, 1984).

Nakamura et al., "Purification and Characterization of a Growth Factor from Rat Platelets for Mature Parenchymal Hepatocytes in Primary Cultures" *Proc. Natl. Acad. Sci, USA* 83(17):6489-6493 (Sep. 1986).

Nakamura et al., "Purification and Subunit Structure of Hepatocyte Growth Factor from Rat Platelets" *FEBS Letters* 224(2):311-316 (Nov. 1987).

Nakatsu et al., "Angiogenic sprouting and capillary lumen formation modeled by human umbilical vein endothelial cells (HUVEC) in fibrin gels: the role of fibroblasts and Angiopoietin-1" *Microvasc Res.* 66(2):102-112 (Sep. 2003).

Naldini et al., "Extracellular Proteolytic Cleavage by Urokinase is Required for Activation of Hepatocyte Growth Factor/Scatter Factor" *EMBO Journal* 11(13):4825-4833 (Dec. 1992).

Naldini et al., "Hepatocyte Growth Factor (HGF) Stimulates the Tyrosine Kinase Activity of the Receptor Encoded by the Proto-Oncogene c-MET" *Oncogene* 6(4):501-504 (Apr. 1991).

Naldini et al., "Scatter Factor and Hepatocyte Growth Factor are Indistinguishable Ligands for the MET Receptor" *EMBO Journal* 10(10):2867-2878 (Oct. 1991).

Novotny et al., "Structural invariants of antigen binding: comparison of immunoglobulin $V_L$-$V_H$ and $V_L$-$V_L$ domain dimers" *Proc. Natl. Acad. Sci. USA* 82(14):4592-4596 (Jul. 1985).

Nygren, H., "Conjugation of Horseradish Peroxidase to Fab Fragments with Different Homobifunctional and Heterobifunctional Cross-Linking Reagents" *The Journal of Histochemsitry and Cytochemistry* 30(5):407-412 (May 1982).

Okajima et al., "Primary Structure of Rat Hepatocyte Growth Factor and Induction of Its mRNA During Liver Regeneration Following Hepatic Injury" *European Journal of Biochemistry* 193(2):375-381 (Oct. 24, 1990).

Okigaki et al., "Functional Characterization of Human Hepatocyte Growth Factor Mutants Obtained by Deletion of Structural Domains" *Biochemistry* 31(40):9555-9561 (Oct. 13, 1992).

Pain et al., "Preparation of Protein A-Peroxidase Monoconjugate Using a Heterobifunctional Reagent, and its Use in Enzyme Immunoassays" *Journal of Immunological Methods* 40(2):219-230 (1981).

Palacios et al., "IL3-Dependent Mouse Clones That Express B-220 Surface Antigen, Contain Ig Genes in Germ-Line Configuration, and Generate B Lymphocytes in Vivo" *Cell* 41(3):727-734 (Jul. 1985).

Park et al., "Sequence of MET Protooncogene cDNA has Features Characteristic of the Tyrosine Kinase Family of Growth-Factor Receptors" *Proc. Natl. Acad. Sci. USA* 84(18):6379-6383 (Sep. 1987).

Parry et al., "The ternary microplasmin-staphylokinase-microplasmin complex is a proteinase-cofactor-substrate complex in action" *Nat. Struct. Biol.* 5(10):917-923 (Oct. 1998).

Peek et al., "Unusual Proteolytic Activation of Pro-hepatocyte Growth Factor by Plama Kallikrein and Coagulation Factor XIa" *Journal of Biological Chemistry* 277(49):47804-47809 (Dec. 6, 2002).

Peisach et al., "Crystal Structure of the Proenzyme Domain of Plasminogen" *Biochemistry* 38(34):11180-11188 (Aug. 24, 1999).
Perona and Craik, "Structural basis of substrate specificity in the serine proteases" *Protein Science* 4(3):337-360 (Mar. 1995).
Ponzetto et al., "A Novel Recognition Motif for Phosphatidylinositol 3-Kinase Binding Mediates Its Association With the Hepatocyte Growth Factor/Scatter Factor Receptor" *Molecular & Cellular Biology* 13(8):4600-4608 (Aug. 1993).
Ponzetto et al., "c-met is Amplified But Not Mutated in a Cell Line with an Activated met Tyrosine Kinase" *Oncogene* 6(4):553-559 (Apr. 1991).
Prat et al., "C-Terminal Truncated Forms of Met, the Hepatocyte Growth Factor Receptor" *Molecular & Cellular Biology* 11(12):5954-5962 (Dec. 1991).
Prat et al., "The Receptor Encoded by the Human c-Met Oncogene is Expressed in Hepatocytes, Epithelial Cells and Solid Tumors" *Int. J. Cancer* 49(3):323-328 (Sep. 30, 1991).
Pratt et al., "The HGF Receptor (Met): Transduction of Signals for Invasive Cell Growth" *Antibody, Immunoconjugates, and Radiopharmaceuticals* 8(4):341-361 (1995).
Presta et al., "Humanization of an Antibody Directed Against IgE" *J. Immunol.* 151(5):2623-2632 (Sep. 1, 1993).
Presta, L., "Antibody Engineering" *Current Opinion in Structural Biology* 2:593-596 (1992).
Rawlings et al., "MEROPS: the protease database" *Nucleic Acids Research* 30(1):343-346 (Jan. 1, 2002).
Renatus et al., "Lysine 156 promotes the anomalous proenzyme activity of tPA: X-ray crystal structure of single-chain human tPA" *EMBO Journal* 16(16):4797-4805 (Aug. 15, 1997).
Richardson et al., "Crystal structure of the human α-thrombin-haemadin complex: an exosite II-binding inhibitor" *EMBO Journal* 19(21):5650-5660 (Nov. 1, 2000).
Riechmann et al., "Reshaping Human Antibodies for Therapy" *Nature* 332:323-327 (Mar. 24, 1988).
Rodrigues et al., "Alternative Splicing Generates Isoforms of the met Receptor Tyrosine Kinase Which Undergo Differential Processing" *Molecular & Cellular Biology* 11(6):2962-2970 (Jun. 1991).
Rubin et al., "A Broad-Spectrum Human Lung Fibroblast-Derived Mitogen is a Variant of Hepatocyte Growth Factor" *Proc. Natl. Acad Sci*, USA 88(2):415-419 (Jan. 15, 1991).
Russell et al., "Partial Characterization of a Hepatocyte Growth Factor From Rat Platelets" *J. Cellular Physiology* 119(2):183-192 (May 1984).
Schlom, J., "Monoclonal Antibodies: They're More and Less Than You Think" *Molecular Foundations of Oncology*, Broder, S. ed., Baltimore, MD:Williams & Wilkins, Chapter 6, pp. 95-134 (1991).
Seki et al., "Isolation and Expression of cDNA for Different Forms of Hepatocyte Growth Factor from Human Leukocyte" *Biochem. and Biophys. Res. Commun.* 172(1):321-327 (Oct. 15, 1990).
Shimomura et al., "Activation of hepatocyte growth factor by two homologous proteases, blood-coagulation factor XIIa and hepatocyte growth factor activator" *European Journal of Biochemistry* 229(1):257-261 (Apr. 1, 1995).
Sims et al., "A Humanized CD18 Antibody Can Block Function Without Cell Destruction" *The Journal of Immunology* 151(4):2296-2308 (Aug. 15, 1993).
Smith et al., "Cardiac Glycoside-Specific Antibodies in the Treatment of Digitalis Intoxication" *Antibodies in Human Diagnosis and Therapy* pp. 365-389 (1977).
Stamos et al., "Crystal structure of the HGF beta-chain in complex with the Sema domain of the Met receptor" *EMBO Journal* 23(12):2325-2335 (Jun. 16, 2004).
Stoker et al., "Scatter Factor is a Fibroblast-Derived Modulator of Epithelial Cell Mobility" *Nature* 327(6119):239-242 (May 21, 1987).
Stubbs & Bode, "A Player of many parts: The Spotlight falls on thrombin's structure" *Thrombosis Research* 69(1):1-58 (Jan. 1993).
Sunitha et al., "Hepatocyte Growth Factor Stimulates Invasion Across Reconstituted Basement Membranes by a New Human Small Intestinal Cell Line" *Clin. Exp. Metastasis* 12(2):143-154 (Mar. 1994).
Takeuchi et al., "Reverse biochemsitry: Use of macromolecular protease inhibitors to dissect complex biological processes and identify a membrane-type serine protease in epithelial cancer and normal tissue" *Proc. Natl. Acad. Aci. USA* 96(20):11054-11061 (Sep. 28, 1999).
Tashiro et al., "Deduced Primary Structure of Rat Hepatocyte Growth Factor and Expression of the mRNA in Rat Tissues" *Proc. Natl. Acad. Sci. USA* 87(8):3200-3204 (Apr. 1990).
Trusolino et al., "Interactions between scatter factors and their receptors: hints for therapeutic applications" *FASEB J.* 12(13):1267-1280 (Oct. 1998).
Trusolino et al., "Scatter-factor and semaphorin receptors: cell signalling for invasive growth" *Nat Rev Cancer* 2(4):289-300 (Apr. 2, 2002).
Tsiang et al., "Functional Mapping of the Surface Residues of Human Thrombin" *J Biol Chem.* (1: J Biol Chem. Jul. 14, 1995;270(28):16854-63) 270(28):16854-16863 (Jul. 14, 1995).
Upstate Biotechnology Inc. *Anti-human Met Monoclonal Antibodies* (product literature).
Verhoeyen et al., "Reshaping Human Antibodies: Grafting an Antilysozyme Activity" *Science* 239:1534-1536 (Mar. 25, 1988).
Vijayalakshmi et al., "The isomorphous structures of prethrombin2, hirugen-, and PPACK-thrombin: Changes accompanying activation and exosite binding to throbmin" *Protein Sci.* 3(12):2254-2271 (Dec. 1994).
Wang et al., "Bovine Chymotrypsinogen A: X-ray Crystal Structure Analysis and Refinement of a new crystal form at 1-8 A Resolution" *J. Mol. Biol.* 185(3):595-624 (Oct. 5, 1985).
Wang et al., "Macrophage Stimulating Protein (MSP) Binds to Its Receptor via the MSP β Chain" *Journal of Biological Chemistry* 272(27):16999-17004 (Jul. 4, 1997).
Weidner et al., "Scatter Factor: Molecular Characteristics and Effect on the Invasiveness of Epithelial Cells" *Journal of Cell Biology* 111(5 Pt 1):2097-2108 (Nov. 1990).
Yamada et al., "Immunohistochemistry with Antibodies to Hepatocyte Growth Factor and its Receptor Protein (c-MET) in Human Brain Tissues" *Brain Research* 637(1-2):308-312 (Feb. 21, 1994).
Zola, H., "Using Monoclonal Antibodies: Soluble Antigens" *Monoclonal Antibodies: A Manual of Techniques*, CRC Press, Chapter 6, pp. 147-158 (1987).
Kirchhofer et al., "Structural and Functional Basis of the Serine Protease-like Hepatocyte Growth Factor β-Chain in Met Binding and Signaling" *Journal of Biological Chemistry* 279:39915-39924 (2004).
Lee et al., "Lack of Critical Domains in the β-Chain of Hepatocyte Growth Factor" *Biochemical and Biophysical Research Communications* 210:1017-1024 (1995).
Lokker et al., "Structure-Function Analysis of Hepatocyte Growth Factor: Identification of Variants that Lack Mitogenic Activity Yet Retain High Affinity Receptor Binding" *EMBO Journal* 11(7):2503-2510 (1992).

* cited by examiner

| HGF | Chymotrypsinogen | Mutation | MDA-MB435 Cell Migration | Cell Migration | n | HGF β/MetIgG | n |
|---|---|---|---|---|---|---|---|
| No. | No. | | % wt | SD | | Binding | |
| | | | | | | IC50mut/IC50wt | |
| | | | | | | (C604S bkgd) | |
| | | | | | | | |
| WT | | | 100 | | | 1 | |
| V495 | *16* | *deletion* | 20.0 | 8.7 | 6 | *>100* | 1 |
| | | *Gly* | 0.0 | 13.9 | 6 | *>100* | 3 |
| | | *Ala* | 6.2 | 19.4 | 5 | *>100* | 3 |
| N497 | 18 | Arg | 53.3 | 15.3 | 8 | 1.7 ± 0.4 | 4 |
| | | Lys | 63.5 | 27.1 | 8 | *3.0 ± 0.5* | 4 |
| | | *Phe* | 83.1 | 13 | 8 | *8.1 ± 0.4* | 3 |
| | | Ala | 102.5 | 22.1 | 8 | 1.5 ± 0.2 | 4 |
| | | *Glu* | 87.7 | 15.9 | 8 | *5.8 ± 0.4* | 4 |
| G498 | *19* | *Ile* | -1.1 | 10.8 | 8 | *>100* | 3 |
| | | *Pro* | 18.2 | 12.5 | 8 | *>100* | 3 |
| | | *Val* | -1.2 | 11.9 | 8 | *>100* | 3 |
| | | Ala | 77.4 | 16.3 | 8 | 1.0 ± 0.1 | 3 |
| | | Ser | 82.6 | 28 | 8 | 1.9 ± 0.1 | 3 |
| P500 | 21 | Trp | 79.3 | 18.3 | 8 | 2.3 | 1 |
| | | His | 79.9 | 20.6 | 8 | 1.6 ± 0.3 | 3 |
| | | Glu | 76.1 | 21.1 | 8 | 0.5 ± 0.03 | 3 |
| T501/R502 | 22/23 | Arg501a/ Ser501b ins | | | | 1.4 ± 0.3 | 3 |
| R502 | 23 | Arg502 del | 77.5 | 15.1 | 8 | 1 ± 0.1 | 3 |
| R502/T503 | 23 | *Arg502/ Thr503 del* | | | | *12 ± 1* | 3 |
| D672 | 194 | *Asn* | -2.0 | 14.3 | | *57 ± 5* | 3 |

*FIG. 1A*

| Binding of Full-length HGF Mutants to Met in Competition Binding Assay ||
|---|---|
| HGF Mutant [Chymotrypsinogen Numbering] | HGF/Met Competition Binding $IC_{50(mut)}/IC_{50(wt)}$ |
| WT | 1 |
| V495A [c16] | 0.8 ± 0.1 |
| V495G [c16] | 1.7 ± 0.1 |
| V495del [c16del] | 0.7 ± 0.2 |
| D672N [c194] | 2.0 ± 0.8 |
| G498A [c19] | 0.7 ± 0.2 |
| G498I [c19] | 1.1 ± 0.5 |
| G498P [c19] | 1.1 ± 0.02 |
| G498V [c19] | 1.3 ± 0.4 |

FIG. 1B

| Inhibition of MDA-MB435 Cell Migration and BxPC3 Proliferation by Full-length HGF Mutants (n=4) ||||
|---|---|---|---|
| HGF Mutant | MDA-MB435 Migration | BxPC3 Proliferation ||
|  | 200 nM HGFmut | 20 nM HGFmut | 200 nM HGFmut |
|  | % of Control ± SD | % of Control ± SD | % of Control ± SD |
| V495G | 28.0 ± 19.5 | 63.4 ± 15.5 | -5.3 ± 6.6 |
| D672N | 26.0 ± 7.4 | 57.4 ± 14.1 | 4.4 ± 9.3 |
| G498I | 21.1 ± 17.6 | 38.5 ± 20.7 | -12.0 ± 11.2 |
| scHGF | 15.2 ± 6.1 | 46.5 (n=2) | 9.3 (n=2) |

FIG. 1C

HGF BETA CHAIN VARIANTS

RELATED APPLICATIONS

This application is a non-provisional application filed under 37 CFR 1.53(b)(1), claiming priority under 35 USC 119(e) to provisional application No. 60/671,610 filed Apr. 15, 2005, the contents of which are incorporated herein in their entirety by reference.

TECHNICAL FIELD

The present invention relates generally to the fields of molecular biology and growth factor regulation. More specifically, the invention concerns modulators of the HGF/c-met signaling pathway, and uses of said modulators.

BACKGROUND

Hepatocyte growth factor (HGF), also known as scatter factor (SF), is the ligand for Met (Bottaro et al., 1991), a receptor tyrosine kinase encoded by the c-met protooncogene (Cooper et al., 1984a &b). HGF binding to Met induces phosphorylation of the intracellular kinase domain resulting in activation of a complex set of intracellular pathways that lead to cell growth, differentiation and migration in a variety of cell types; several recently published reviews provide a comprehensive overview (Birchmeier et al., 2003; Trusolino and Comoglio, 2002; Maulik et al., 2002). In addition to its fundamental importance in embryonic development and tissue regeneration, the HGF/Met signaling pathway has also been implicated in invasive tumor growth and metastasis and as such represents an interesting therapeutic target (Birchmeier et al., 2003; Trusolino and Comoglio, 2002; Danilkovitch-Miagkova and Zbar, 2002; Ma et al., 2003).

HGF belongs to the plasminogen-related growth factor family and comprises a 69 kDa α-chain containing the N-terminal finger domain (N) and four Kringle (K1-K4) domains, and a 34 kDa β-chain which has strong similarity to protease domains of chymotrypsin-like serine proteases from Clan PA(S)/FamilyS1 (Nakamura et al., 1989; Donate et al., 1994; Rawlings et al., 2002). Like plasminogen and other serine protease zymogens, HGF is secreted as a single chain precursor form (scHGF). scHGF binds to heparan sulfate proteoglycans, such as syndecan-1 (Derksen et al., 2002) on cell surfaces or in the extracellular matrix. Heparan sulfate proteoglycans bind to the N domain (Hartmann et al., 1998), which also contributes to the high affinity Met binding together with amino acids located in K1 (Lokker et al., 1994). Although scHGF is able to bind Met with high affinity, it cannot activate the receptor (Lokker et al., 1992; Hartmann et al., 1992). Acquisition of HGF signaling activity is contingent upon proteolytic cleavage (activation) of scHGF at Arg494-Val495 resulting in the formation of mature HGF, a disulfide-linked α/β heterodimer (Lokker et al., 1992; Hartmann et al., 1992; Naldini et al., 1992). The protease-like domain of HGF (HGF β-chain) is devoid of catalytic activity since it lacks the required Asp [c102]-His [c57]-Ser [c195] (standard chymotrypsinogen numbering in brackets throughout) catalytic triad found in all serine proteases (Perona and Craik, 1995; Hedstrom, 2002), having a Gln534 [c57] and Tyr673 [c195].

Because of its importance in regulating HGF activity, this process must be tightly controlled by HGF converting enzymes and their corresponding physiological inhibitors. scHGF activation is mediated in vitro by chymotrypsin-like serine proteases including hepatocyte growth factor activator (HGFA) (Miyazawa et al., 1993), matriptase/MT-SP1 (Takeuchi et al. 1999; Lin et al., 1999), urokinase-type plasminogen activator (Naldini et al., 1992), factor XIIa (Shimomura et al., 1995), factor XIa (Peek et al., 2002) and plasma kallikrein (Peek et al., 2002). Similar to scHGF, these proteases are produced as inactive precursors; their enzymatic activities are also tightly regulated by other activating proteases and both Kunitz- and serpin-type inhibitors.

Serine proteases and their activation process have been described (Donate et al., 1994). In serine proteases, activation cleavage of the zymogen effects a conformational rearrangement of the so-called 'activation domain' giving rise to a properly formed active site and the substrate/inhibitor interaction region. The activation domain constitutes three surface-exposed loops designated the [c140]-, [c180]- and [c220]-loops and insertion of the newly formed N-terminus into a hydrophobic pocket (Huber and Bode, 1978). In the homologous ligand/receptor pair macrophage stimulating protein (MSP)/Ron, the serine protease-like MSP β-chain provides the main energy for receptor binding (Wang et al., 1997; Miller and Leonard, 1998). This is reversed from the HGF/Met system where the high affinity receptor binding site for Met resides in the HGF α-chain (Lokker et al., 1994; Okigaki et al., 1992).

The importance of the HGF/Met signaling axis in normal cellular function and in the etiology of clinical disorders suggests the need to develop highly effective therapeutic means based on modulation of this axis. The complexity of this pathway, however, particularly in light of the less well-understood mechanism of HGF-HGF and HGF/Met interactions, has slowed progress on this front and highlighted the need to develop approaches that are based on better understanding of the mechanism of action of the HGF-HGF and HGF/Met interactions. The invention disclosed hereinbelow fulfills this need and provides other benefits.

All references cited herein, including patent applications and publications, are incorporated by reference in their entirety.

DISCLOSURE OF THE INVENTION

Hepatocyte growth factor (HGF), a plasminogen-related growth factor, binds to its receptor tyrosine kinase Met (also referred to herein as C-Met, c-Met or c-met), which is implicated in development, tissue regeneration and invasive tumor growth. The serine protease-like HGF β-chain itself binds to Met. Other than binding to Met, it is not clear what regions and specific residues in the HGF β chain are necessary to effect proper signaling through the HGF/Met pathway. We predicted that certain regions/positions within the β chain make important contributions to proper HGF functional activity, wherein these contributions may or may not involve binding of HGF β chain to its cognate receptor. The results described herein provide evidence that mutations in the N terminal region and/or dimerization region of HGF β chain can disrupt HGF/Met biological function, with or without substantially impairing HGF (in particular HGF β chain) binding to C-Met. In general but not necessarily, these mutations do not implicate positions thought to comprise the 'activation domain' or 'active site region' of wild type HGF.

Mutation analyses described herein provide a basis for design of a multitude of HGF mutants capable of inhibiting wild type HGF/HGF and HGF/c-met interactions across a spectrum of potencies. Examples of such mutants are described herein. These mutants are capable of competing with wild type HGF for binding to c-met, yet exhibit reduced ability to effect c-met associated biological functions. This is particularly advantageous where complete or substantial inhibition of the HGF/c-met axis is undesirable; this is of particular concern because HGF and c-met are ubiquitously expressed in normal cells and tissues. These mutants can also be used as advantageous therapeutic agents for treating pathological conditions wherein reduced, but not complete absence of, HGF/c-met biological activity is desirable. Methods and compositions of the invention are based at least in part on these findings, which are described in greater detail below.

In one aspect, the invention provides an HGF/C-Met antagonist molecule comprising an HGF mutant comprising a mutation in HGF β chain N terminal region and/or HGF β chain dimerization region.

A mutation in the HGF β chain N terminal region can be any that impairs insertion of HGF β chain N-terminus into an HGF binding pocket. In one embodiment, the resulting HGF β chain mutant binds to C-Met with reduced binding affinity compared to wild type HGF β chain. In one embodiment, the resulting HGF β chain mutant binds to C-Met with substantially equivalent affinity as wild type HGF β chain. In one embodiment, the resulting full-length HGF containing a mutated HGF β chain binds to C-Met with reduced binding affinity compared to full-length wild type HGF. In one embodiment, the resulting full-length HGF containing a mutated HGF β chain binds to C-Met with substantially equivalent affinity as full-length wild type HGF. In one embodiment, a mutation is in or adjacent to the P1' position (i.e., 495 [c16]), wherein the mutation results in a cleavable HGF mutant, and wherein the N-terminus of HGF β chain does not insert into an active site/binding pocket. Examples for inability to insert into an active site/binding pocket include, but are not limited, to configurations wherein the mutant is defective in either or both (i) hydrophobic interactions, and (ii) formation of salt bridge involving the N-terminus to Asp672 [c] 194, e.g., where an N-terminus bears a mutation, e.g., a positively-charged substituted or inserted amino acid residue. In one embodiment, signaling via this mutant is impaired. In one embodiment, a mutation is in or adjacent to one or more of positions P1', P2', P3' and P4'.

A mutation in the HGF β chain dimerization domain can be any that would be expected to impair contact between two HGF β chains such that dimerization of the two chains (and thus two HGF molecules) is impaired. Such mutations would be evident from the amino acid structure of HGF complexes, for example, as described in Kirchhofer et al., J Biol Chem. (2004), 279(38):39915-24. Relevant amino acid positions include, but are not limited to, those described herein. In one embodiment, the resulting HGF mutant has reduced ability to dimerize with another HGF β chain. In one embodiment, a mutation in HGF β chain dimerization region does not substantially impair binding of the resulting HGF mutant to C-Met.

Dimerization domain refers to a region of a HGF β chain that interacts with another HGF β chain to form a dimer (e.g., in a HGF/Met activation complex). Upon cleavage of pro-HGF, the HGF β chain undergoes a conformational change. The HGF β chain N-terminal residue 495 forms a salt bridge with residue Asp 672. In some embodiments, the dimerization region of an HGF β comprises, consists essentially of, or consists of at least one amino acid residue (up to all amino acid residues) corresponding to residues of HGF β from about 495 to 502, the [c140 loop] amino acids including Y619, T620, G621, the [c180] loop amino acids including 662 to 665, or mixtures thereof. In one embodiment, the dimerization domain includes positions located close/adjacent to one or more of the positions listed above and thus are predicted to influence said one or more positions. For example, in this embodiment, the dimerization domain may further include positions 622 and 626.

In one aspect, an HGF/Met antagonist molecule of the invention comprises a mutation in HGF β chain N terminal region, wherein the mutation is in position V495, G498, R502 plus T503, and/or D672. A mutation can be in any form that alters the primary, secondary and/or tertiary structure of the N terminal region of HGF β chain. For example, in one embodiment, a mutation in HGF β chain N terminal region is a substitution, insertion and/or deletion, such as V495G, V495A, G498I, G498P, G498V, R502del plus T503del, or D672N. In another embodiment, a mutation in HGF β chain N terminal region is a deletion of V495. A mutation that alters the primary, secondary and/or tertiary structure of the N terminal region of HGF β chain can also be in an amino acid position that is not in the HGF β chain N terminal region itself. For example, a mutation of D672 that removes salt bridge formation (e.g., D672N) with HGF β chain N terminus would also be expected to alter the primary, secondary and/or tertiary structure of the HGF β chain N terminal region. Thus, mutations of the HGF β chain N terminal region and HGF β chain dimerization region are not necessarily mutually exclusive. For example, as described herein, and exemplified in FIG. 1, mutation in certain positions may be expected to affect both the N terminal and dimerization domains of HGF β chain.

In one aspect, an HGF/Met antagonist molecule of the invention comprises a mutation in HGF β chain dimerization domain, wherein the mutation is in position N497, G498, P500, at or adjacent to T501 and R502, or R502. A mutation can be in any form that alters the primary, secondary and/or tertiary structure of the dimerization region of HGF β chain. Examples of mutations that would alter the structure of the dimerization region of the HGF β chain include mutations that introduce a residue that is charged or has a large side-chain (e.g., bulky) into the wild-type sequence, whereby a charged residue may result in repulsive interactions and a large side chain may result in adverse steric interactions. Furthermore, cysteine mutations (e.g., L622C, I664C, P500C, and N497C) can also be introduced that are available for modification by specific thiol alkylating reagents such as those containing maleimide and haloacetyl groups. In one embodiment, a mutation in HGF β chain dimerization region is a substitution, insertion and/or deletion, such as N497R or K; G498A or S; P500W, H or E; insertion between T501 and R502 (e.g., an insertion of R and/or S); or R502del. In one embodiment, a mutation at position N497 is not N497F, A or E. In one embodiment, a mutation is in one or more of positions 495 to 503, wherein such a mutation could alter HGF β chain dimerization and/or binding to receptor. In another embodiment, mutations that affect the dimerization domain can be combined with mutation in one or more positions outside of the dimerization domain, e.g., a mutation at or adjacent to the 494-495 cleavage site. For example, in a mutant that would be expected to be noncleavable (e.g. R494E:V495G double mutant) and that also contains a mutation in the dimerization domain, such a mutant would nonetheless exhibit impaired biological function even if does get cleaved in vivo.

In some embodiments of an HGF/Met antagonist molecule of the invention, the molecule comprises wild type amino acids at position 534, 578, 619, 673, 692, 693, 694, 695, 696, 699, and/or 702. In some embodiments of HGF/Met antagonists of the invention, the antagonists comprise mutations at position L622 (e.g., L622C or K); I623 (e.g., I623C); D626 (e.g., D626K); L622 plus D626 (e.g., L622K plus D626K);

K663 (e.g., K663C); I664 (e.g., I664C); R502 (e.g., 502C); P500 (e.g., P500C); N497 (e.g., N497C); R494 plus I623 (e.g., R494E plus I623C); N497 plus G498 (e.g., N497R plus G498A, or N497K plus G498A); N497 plus P500 (e.g., N497R plus P500H, or N497K plus P500H); G498 plus P500 (e.g., G498A plus P500H); N497 plus G498 plus P500 (e.g., N497R plus G498A plus P500H, or N497K plus G498A plus P500H); N497 plus L622 (e.g., N497R plus L622K, or N497K plus L622K); N497 plus D626 (e.g., N497R plus D626K, or N497K plus D626K); N497 plus L622 plus D626 (e.g., N497R plus L622K plus D626K, or N497K plus L622K plus D626K).

In one embodiment, an HGF/Met antagonist molecule of the invention comprises a mutation in the HGF active site alone or in combination with one or more of the mutations described herein. Mutations of the active site include mutations at position 667 and/or 704. Suitable mutations include substitution of one or both of these positions with a C or a W.

In general, an HGF/Met antagonist molecule of the invention comprises an HGF molecule having a mutation in the HGF β chain that reduces one or more of the biological characteristics normally associated with wild type HGF. For example, in one embodiment, the molecule has reduced C-Met signaling capability (e.g., Met phorphorylation) compared to wild type HGF. In another embodiment, the molecule has reduced ability to stimulate cell migration compared to wild type HGF. In another embodiment, the molecule has reduced ability to stimulate cell proliferation compared to wild type HGF. In another embodiment, the molecule has reduced ability to stimulate angiogenesis compared to wild type HGF. An HGF/Met antagonist molecule of the invention generally comprises at least a portion of the HGF α chain that is involved in binding to Met, linked to a mutated HGF β chain as described herein.

As shown by the mutational analysis described herein, certain regions, and specific amino acid positions therein, in HGF β chain play important roles in modulating HGF biological functions. Accordingly, in one aspect, the invention also provides HGF/Met modulators that specifically target these regions. Such modulators include nucleic acids such as aptamer, and polypeptides such as binding peptides and antibodies.

As used herein, the letter before a number indicates the corresponding wild type amino acid found at the amino acid position denoted by that number in a wild type human HGF polypeptide, and the letter(s) (if present) after the number indicates the mutation type/amino acid (e.g., substitution amino acid, deletion (del) or insertion (ins)).

In one aspect, the invention provides an HGF mutant that has HGF/c-met modulatory activity, e.g. an antagonist of HGF/c-met activity or an HGF variant exhibiting a reduction, but not an absence, of HGF biological activity (e.g., cell growth stimulatory activity). In one embodiment, an antagonist of the invention is capable of inhibiting the biological activity of wild type HGF in vivo or in vitro (such biological activity includes but is not limited to receptor phosphorylation, stimulation of cell proliferation, enhancement of cell survival, promotion of angiogenesis, induction/promotion of cell migration). In one embodiment, an HGF mutant provides reduced cell growth promoting activity (e.g., cell proliferation, cell survival, angiogenic, cell migration).

In one embodiment, an antagonist molecule of the invention competes with wild type HGF for binding to Met. In some of the embodiments, said molecule inhibits c-met receptor multimerization (e.g., dimerization). In some embodiments, said molecule comprises a variant (mutant) β chain having reduced ability to interact (e.g., multimerize/dimerize) with another β chain molecule. In some embodiments, said molecule inhibits HGF β chain multimerization (e.g., dimerization). In some embodiments, said molecule binds to c-met but exhibits reduced ability to effect c-met activation (e.g., as indicated by reduced c-met phosphorylation, mitogen activated protein kinase (MAPK) phosphorylation, and/or reduced HGF/c-met dependent cell migration, cell proliferation, cell survival, cell morphogenesis, angiogenesis etc.).

In any molecule of the invention wherein one or more positions is mutated relative to the wild type counterpart sequence, the mutation can be of any form that alters the functional effect of the corresponding wild type residue. A mutation can be obtained in any suitable form known in the art (and/or determined empirically), e.g. by substitution, insertion, addition and/or deletion. In some embodiments, a mutation comprises a non-conservative substitution. Suitable substitutions include but are not limited to those described herein (in particular in the Examples), e.g. with amino acids such as alanine and serine.

In one aspect, a molecule/substance (e.g., HGF/c-met modulators as described herein) is linked to a toxin such as a cytotoxic agent. These molecules/substances can be formulated or administered in combination with an additive/enhancing agent, such as a radiation and/or chemotherapeutic agent.

The invention also provides methods and compositions useful for modulating disease states associated with dysregulation of the HGF/c-met signaling axis. Thus, in one aspect, the invention provides a method of modulating c-met activation in a subject, said method comprising administering to the subject an HGF/c-met antagonist molecule of the invention, whereby c-met activation is modulated. In one embodiment, said molecule is an HGF/c-met antagonist that inhibits HGF/c-met activity. In one embodiment, said antagonist inhibits specific binding of wild type HGF β to c-met. In one aspect, the invention provides a method of treating a pathological condition associated with activation of c-met in a subject, said method comprising administering to the subject a c-met antagonist of the invention, whereby c-met activation is inhibited.

The HGF/c-met signaling pathway is involved in multiple biological and physiological functions, including, e.g., cell growth stimulation (e.g. cell proliferation, cell survival, cell migration, cell morphogenesis) and angiogenesis. Thus, in another aspect, the invention provides a method of inhibiting c-met activated cell growth (e.g. proliferation and/or survival), said method comprising contacting a cell or tissue with an antagonist of the invention, whereby cell proliferation associated with c-met activation is inhibited. In yet another aspect, the invention provides a method of inhibiting angiogenesis, said method comprising administering to a cell, tissue, and/or subject with a condition associated with abnormal angiogenesis an HGF/Met antagonist of the invention, whereby angiogenesis is inhibited.

In one aspect, the invention provides use of an antagonist of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder. The antagonist can be of any form described herein, including antibody, antibody fragment, polypeptide (e.g., an oligopeptide, HGF polypeptide mutant/variant), nucleic acid (aptamer), or combination thereof.

In one aspect, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a host cell of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides a method of inhibiting c-met activated cell proliferation, said method comprising contacting a cell or tissue with an effective amount of an antagonist of the invention, whereby cell proliferation associated with c-met activation is inhibited.

In one aspect, the invention provides a method of treating a pathological condition associated with dysregulation of c-met activation in a subject, said method comprising administering to the subject an effective amount of an antagonist of the invention, whereby said condition is treated.

In one aspect, the invention provides a method of inhibiting the growth of a cell that expresses c-met or hepatocyte growth factor, or both, said method comprising contacting said cell with a c-met antagonist of the invention thereby causing an inhibition of growth of said cell. In one embodiment, the cell is contacted by HGF expressed by a different cell (e.g., through a paracrine effect).

In one aspect, the invention provides a method of therapeutically treating a mammal having a cancerous tumor comprising a cell that expresses c-met or hepatocyte growth factor, or both, said method comprising administering to said mammal an effective amount of an antagonist of the invention, thereby effectively treating said mammal. In one embodiment, the cell is contacted by HGF expressed by a different cell (e.g., through a paracrine effect).

In one aspect, the invention provides a method for treating or preventing a cell proliferative disorder associated with increased expression or activity of c-met or hepatocyte growth factor, or both, said method comprising administering to a subject in need of such treatment an effective amount of an antagonist of the invention, thereby effectively treating or preventing said cell proliferative disorder. In one embodiment, said proliferative disorder is cancer.

In one aspect, the invention provides a method for inhibiting the growth of a cell, wherein growth of said cell is at least in part dependent upon a growth potentiating effect of c-met or hepatocyte growth factor, or both, said method comprising contacting said cell with an effective amount of an antagonist of the invention, thereby inhibiting the growth of said cell. In one embodiment, the cell is contacted by HGF expressed by a different cell (e.g., through a paracrine effect).

In one aspect, the invention provides a method of therapeutically treating a tumor in a mammal, wherein the growth of said tumor is at least in part dependent upon a growth potentiating effect of c-met or hepatocyte growth factor, or both, said method comprising contacting said cell with an effective amount of an antagonist of the invention, thereby effectively treating said tumor. In one embodiment, the cell is contacted by HGF expressed by a different cell (e.g., through a paracrine effect).

Methods of the invention can be used to affect any suitable pathological state, for example, cells and/or tissues associated with dysregulation of the HGF/c-met signaling pathway. In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell (e.g., of the thyroid gland), a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, a multiple myeloma cell, and a leukemia cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent. In one embodiment, an HGF/Met antagonist molecule of the invention is administered to a subject in combination with one or more other therapeutic agent, for example erlotinib (TARCEVA®), pemetrexed (ALIMTA®), bevacizumab (AVASTIN®), gefitinib (IRESSA®), trastuzumab (HERCEPTIN®), and rituximab (RITUXAN®). Administration of therapeutic agents in combination therapy can occur concurrently or sequentially.

As described herein, c-met activation is an important biological process the dysregulation of which leads to numerous pathological conditions. Accordingly, in one embodiment of methods of the invention, a cell that is targeted (e.g., a cancer cell) is one in which activation of c-met is enhanced as compared to a normal cell of the same tissue origin. In one embodiment, a method of the invention causes the death of a targeted cell. For example, contact with an antagonist of the invention may result in a cell's inability to signal through the c-met pathway, which results in cell death.

Dysregulation of c-met activation (and thus signaling) can result from a number of cellular changes, including, for example, overexpression of HGF (c-met's cognate ligand) and/or c-met itself. Accordingly, in some embodiments, a method of the invention comprises targeting a cell wherein c-met or hepatoctye growth factor, or both, is more abundantly expressed by said cell (e.g., a cancer cell) as compared to a normal cell of the same tissue origin. A c-met-expressing cell can be regulated by HGF from a variety of sources, i.e. in an autocrine or paracrine manner. For example, in one embodiment of methods of the invention, a targeted cell is contacted/bound by hepatocyte growth factor expressed in a different cell (e.g., via a paracrine effect). Said different cell can be of the same or of a different tissue origin. In one embodiment, a targeted cell is contacted/bound by HGF expressed by the targeted cell itself (e.g., via an autocrine effect/loop).

In some embodiments, HGF/Met antagonists of the invention comprise HGF mutants that comprise modifications that enhance their inhibitory and/or therapeutic effect (including, e.g., enhanced affinity, improved pharmacokinetics properties (such as half life, stability, clearance rate), reduced toxicity to the subject). Such modifications include, e.g., modifications involving glycosylation, pegylation, substitution with non-naturally occurring but functionally equivalent amino acid, linking groups, etc. Suitable modifications are well known in the art, and furthermore can be determined empirically as necessary.

In one aspect, the invention provides compositions comprising one or more HGF/c-met antagonists of the invention and a carrier. In one embodiment, the carrier is pharmaceutically acceptable.

In one aspect, the invention provides nucleic acids encoding a HGF/c-met antagonist of the invention. In one embodiment, a nucleic acid of the invention encodes a HGF/c-met antagonist which is or comprises a polypeptide (e.g., an HGF mutant/variant). In one embodiment, a nucleic acid of the invention encodes a HGF/c-met antagonist which is or comprises an antibody or fragment thereof.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, E. coli. In one embodiment, a host cell is a eukaryotic cell, for example a mammalian cell such as Chinese Hamster Ovary (CHO) cell.

In one aspect, the invention provides methods for making a HGF/c-met antagonist of the invention. For example, the invention provides a method of making an antagonist which is or comprises an antibody (or fragment thereof), said method comprising expressing in a suitable host cell a recombinant vector of the invention encoding said antibody (or fragment thereof), and recovering said antibody. In another example, the invention provides a method of making a HGF/c-met antagonist which is or comprises a polypeptide (such as an HGF mutant/variant), said method comprising expressing in a suitable host cell a recombinant vector of the invention encoding said polypeptide, and recovering said polypeptide.

In one aspect, the invention provides an article of manufacture comprising a container; and a composition contained within the container, wherein the composition comprises one or more HGF/c-met antagonists of the invention. In one embodiment, the composition comprises a nucleic acid of the invention. In one embodiment, a composition comprising a HGF/c-met antagonist further comprises a carrier, which in some embodiments is pharmaceutically acceptable. In one embodiment, an article of manufacture of the invention further comprises instructions for administering the composition to a subject.

In one aspect, the invention provides a kit comprising a first container comprising a composition comprising one or more HGF/c-met antagonists of the invention; and a second container comprising a buffer. In one embodiment, the buffer is pharmaceutically acceptable. In one embodiment, a composition comprising an HGF/c-met antagonist further comprises a carrier, which in some embodiments is pharmaceutically acceptable. In one embodiment, a kit further comprises instructions for administering the composition to a subject.

BRIEF DESCRIPTION OF THE DRAWINGS

FIG. 1(A) depicts characterization of various HGF mutants. Both HGF β chain N-terminal insertion and HGF β chain dimerization mutants are exemplified. "Cell Migration" data relate to migration of MDA-MB435 cells in the presence of full-length HGF containing the indicated mutation(s), expressed as percentage of migration in the presence of wild-type HGF. "HGF β/MetIgG Binding" data relate to binding of HGF β chain (containing the indicated mutation(s)) to MetIgG, expressed as the ratio of $IC_{50}$ (mutant) to $IC_{50}$ (wild-type) in a competition binding assay. In these data, WT refers to the C604S mutant; HGF β mutants also contained this mutation. Note: As a general reference, mutations are indicated in bold if they are expected to disrupt potential β chain-β chain interactions, and mutations are indicated in italics and underlined (bold or unbold) if they are expected to disrupt insertion of the N-terminus. These expectations are based on the predominant effect observed or expected for the respective mutations—i.e., effect on either β chain-β chain interactions or ability of the β chain N-terminus to insert into an active site/binding pocket. Notwithstanding this, the skilled practitioner would readily be able to determine whether a particular mutation would have one or both effects, whether indicated as such or not in FIG. 1A. For example, in some instances, a mutation may affect both β chain-β chain interactions and insertion of the N-terminus, or in some instances a mutation indicated in FIG. 1A as expected to affect β chain-β chain interactions may empirically be shown to affect insertion of the N-terminus. Similarly, apparently "impaired" Met binding values are indicated in italics, and apparently "normal" binding values are indicated in bold text, although the degree of "impairment" and "normality" is relative.

(B) Binding of full-length HGF containing the indicated mutation(s) to Met as measured in a competition binding assay. Data are expressed as the ratio of $IC_{50}$ (mut) to $IC_{50}$ (wild-type).

(C) Inhibition of cell migration and proliferation by full-length HGF containing the indicated mutation(s). Amount of cell migration and proliferation activity, respectively, in the presence of mutant HGF and wild-type HGF (1 nM wild type HGF for migration; 0.25 nM wild type HGF for proliferation) is expressed as a percentage of activity observed in the presence of wild type HGF alone.

Figure 2A:
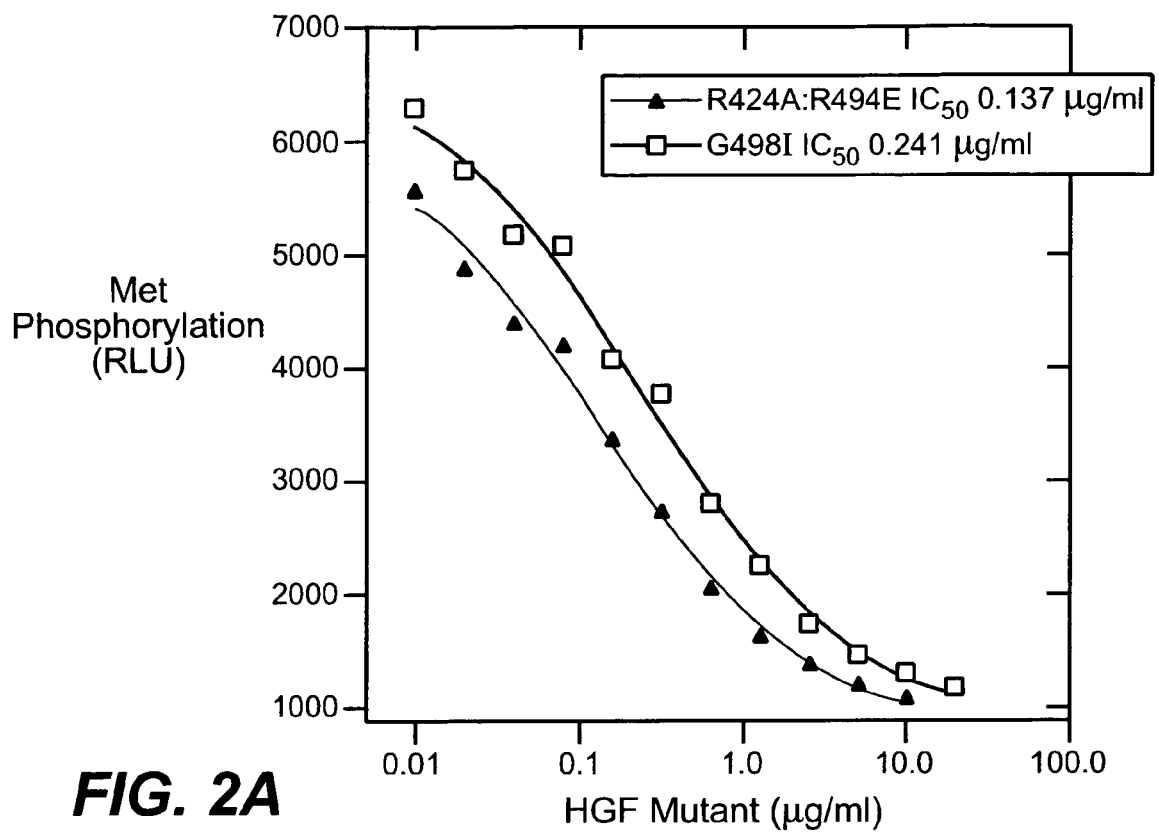

FIG. 2(A) Inhibition of HGF-dependent Met phosphorylation in A549 cells by HGF mutants as indicated; R424A: R494E refers to single-chain HGF. Amount of Met phosphorylation is indicated as RLU (relative light unit). (B) Inhibition of HGF-dependent Met phosphorylation in A549 lung carcinoma cells by HGF mutants as indicated. Amount of Met phosphorylation is indicated as a percentage of control (which is the amount observed in the presence of 0.5 nM wild-type HGF).

Figure 3A:
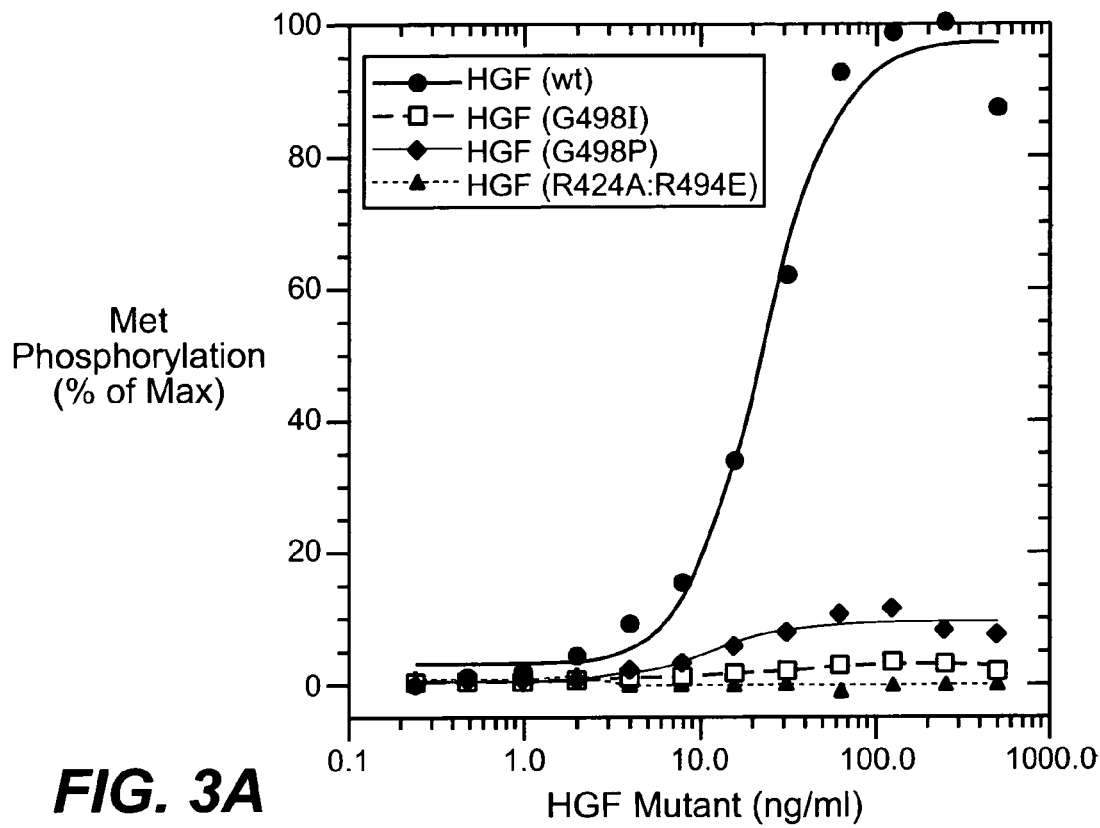

FIGS. 3(A) and (B) Phosphorylation of Met in A549 cells in the presence of wild-type and mutant HGF. Amount of Met phosphorylation is indicated as a percentage of maximum phosphorylation observed in the presence of wild type HGF at each of the respective wild-type HGF concentrations.

Figure 4:
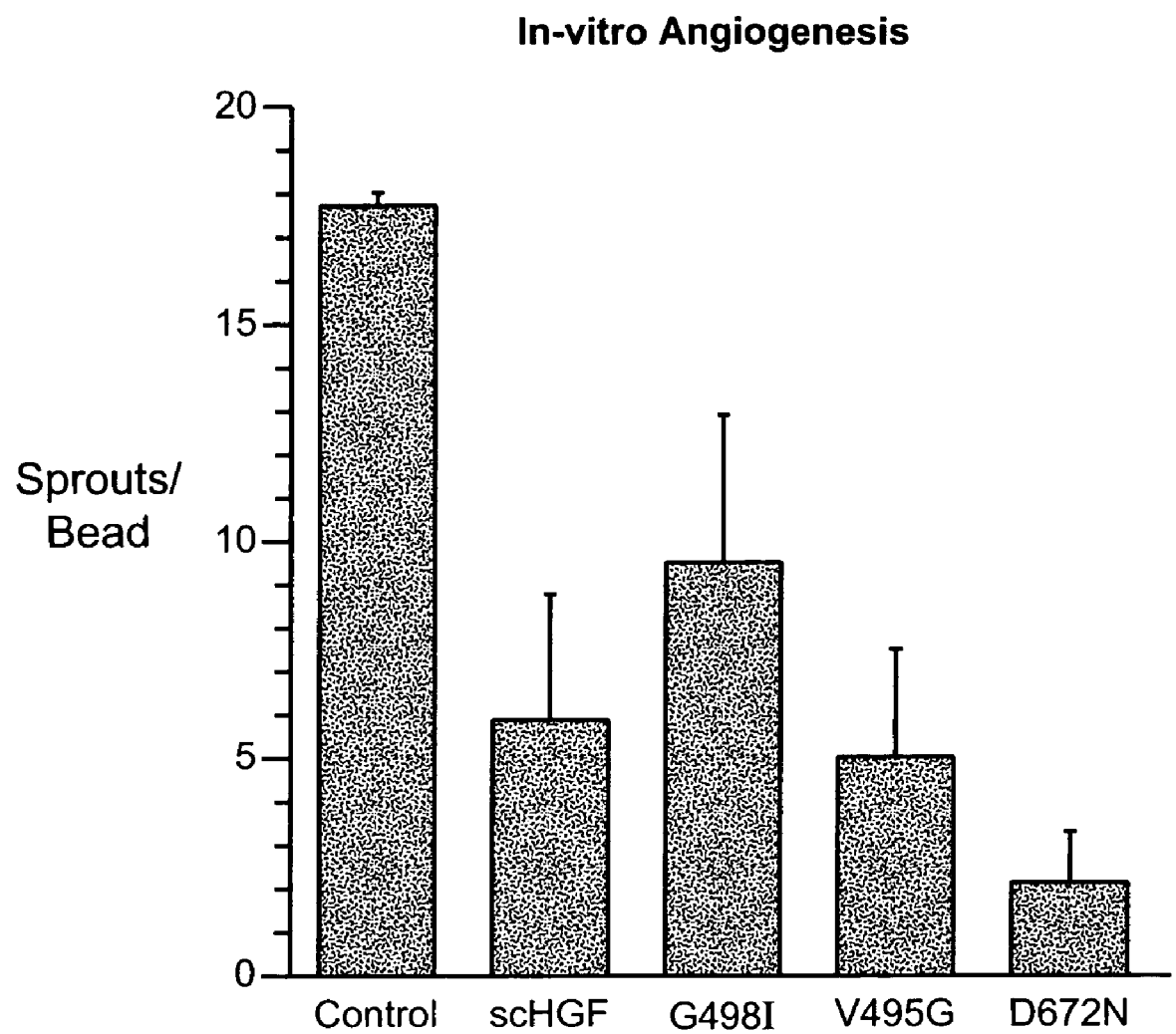

FIG. 4 Angiogenic activity in the presence of mutant HGF. Amount of angiogenesis is indicated as number of sprouts/bead in the presence of HGF mutants as indicated.

MODES FOR CARRYING OUT THE INVENTION

The invention provides methods, compositions, kits and articles of manufacture for modulating the HGF/c-met signaling pathway.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988).

Definitions

As employed herein, references to amino acid names may be the art-accepted designations in one or more of the following forms, all of which are used interchangeably herein: (i) full name (e.g., tryptophan, serine, glycine, etc.), (ii) three-letter abbreviations (e.g., Trp, Ser, Gly, etc.), and (iii) one-letter designations (e.g., W, S, G, etc.).

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, as described in U.S. Pat. No. 6,828,146.

As used herein, the terms "peptide" and "polypeptide" are used interchangeably, except that the term "peptide" generally refers to polypeptide comprising fewer than 200 contiguous amino acids. The term "peptide" generally refers to a contiguous and relatively short sequence of amino acids linked by peptidyl bonds. Typically, but not necessarily, a peptide has a length of about 2 to 50 amino acids, 4-40 amino acids or 10-30 amino acids.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl.

Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "hepatocyte growth factor" or "HGF", as used herein, refers, unless specifically indicated otherwise, to any native or variant (whether native or synthetic) HGF polypeptide that is capable of activating the HGF/c-met signaling pathway under conditions that permit such process to occur. The term "wild type HGF" generally refers to a polypeptide comprising the amino acid sequence of a naturally occurring HGF protein. Thet term "wild type HGF sequence" generally refers to an amino acid sequence found in a naturally occurring HGF.

The phrase "does not substantially impair", "does not substantially reduce", "are substantially similar" or "are substantially equivalent", and variations thereof, as used herein, denotes a sufficiently high degree of similarity between two numeric values such that one of skill in the art would consider the difference between the two values to be of little or no biological significance within the context of the biological characteristic measured by said values. The difference between said two values is preferably less than about 50%, preferably less than about 40%, preferably less than about 30%, preferably less than about 20%, preferably less than about 10%. Examples of "two numeric values" include a value associated with a wild type protein and a value associated with a mutated form of said protein.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813(1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

A "disorder" or "pathological condition" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors or cancers; non-leukemias and lymphoid malignancies; neuronal, glial, astrocytal, hypothalamic and other glandular, macrophagal, epithelial, stromal and blastocoelic disorders; and inflammatory, immunologic, neurodegenerative disorders, angiogenesis-related disorders and disorders related to mitochondrial or metabolic defects.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include multiple myeloma, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer (e.g., renal cell carcinoma), liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid; capecitabine; and pharmaceutically acceptable salts, acids or derivatives of any of the above.

Also included in the definition of "chemotherapeutic agent" above are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth inhibitory agent" when used herein refers to a compound or composition which inhibits growth of a cell whose growth is dependent upon HGF/c-met activation either in vitro or in vivo. Thus, the growth inhibitory agent may be one which significantly reduces the percentage of HGF/c-met-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-$\alpha$-L-lyxo-hexapyranosyl)oxy]-7,8,9,10-tetrahydro-6,8,11-trihydroxy-8-(hydroxyacetyl)-1-methoxy-5,12-naphthacenedione.

HGF/Met Antagonists—Peptides/Polypeptides (Including Antibodies)

One aspect of the invention pertains to isolated peptide/polypeptide and antibody modulators of HGF $\beta$ chain-$\beta$ chain interaction and HGF-Met interaction. In one embodiment, modulators (such as peptides/polypeptides and antibodies) can be isolated from cells or tissue sources by an appropriate purification scheme using standard protein purification techniques. In another embodiment, the modulators are produced by recombinant DNA techniques. As an alternative to recombinant expression, modulators can be synthesized chemically using standard peptide synthesis techniques.

HGF/Met antagonist molecules of the invention include those described in FIG. 1. The invention also provides a mutant or variant protein any of which residues may be changed from the corresponding residues of these peptides/polypeptides, while still encoding a peptide/polypeptide that maintains modulatory activity. In one embodiment, a variant of a peptide/polypeptide antagonist has at least 50%, 60%, 70%, 80%, 90%, 95%, 98%, 99% amino acid sequence identity with the sequence of a reference peptide/polypeptide antagonist. In general, the variant exhibits substantially the same or greater binding affinity than the reference binder peptide/polypeptide antagonist, e.g., at least 0.75×, 0.8×, 0.9×, 1.0×, 1.25× or 1.5× the binding affinity of the reference binder peptide/polypeptide/ligand, based on an art-accepted binding assay quantitation unit/metric, while retaining a desirable degree of antagonist activity.

In general, variants of the invention include variants in which residues at a particular position in the sequence have been substituted by other amino acids, and further includes the possibility of inserting an additional residue or residues between two residues of the parent protein/peptide as well as the possibility of deleting one or more residues from the parent sequence or adding one or more residues to the parent sequence. Any amino acid substitution, insertion, or deletion is encompassed by the invention. In favorable circumstances, the substitution is a conservative substitution as described herein.

An "isolated" or "purified" peptide, polypeptide, protein or biologically active fragment is separated and/or recovered from a component of its natural environment. Contaminant components include materials that would typically interfere with diagnostic or therapeutic uses for the polypeptide, and may include enzymes, hormones, and other proteinaceous or non-proteinaceous materials. Preparations having preferably less than 30% by dry weight of non-desired contaminating material (contaminants), preferably less than 20%, 10%, and preferably less than 5% contaminants are considered to be substantially isolated. An isolated, recombinantly-produced peptide/polypeptide or biologically active portion thereof is preferably substantially free of culture medium, i.e., culture medium represents preferably less than 20%, preferably less than about 10%, and preferably less than about 5% of the volume of a peptide/polypeptide preparation. Examples of contaminants include cell debris, culture media, and substances used and produced during in vitro synthesis of the peptide/polypeptide.

Conservative substitutions of peptides/polypeptides are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr; cys | cys |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the peptide/polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Variants of antibody modulators can also be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an FcγR may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an FcγRI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an FcγRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an FcγRIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in WO99/51642. Such variants may comprise an amino acid substitution at one or more of amino acid positions 270, 322, 326, 327, 329, 331, 333 or 334 of the Fc region. See, also, Duncan & Winter *Nature* 322:738-40 (1988); U.S. Pat. No. 5,648,260; U.S. Pat. No. 5,624,821; and WO94/29351 concerning Fc region variants.

Vector Construction

Polynucleotide sequences encoding the peptides/polypeptides described herein can be obtained using standard recombinant techniques. Desired polynucleotide sequences may be isolated and sequenced from appropriate source cells. Source cells for antibodies would include antibody producing cells such as hybridoma cells. Alternatively, polynucleotides can be synthesized using nucleotide synthesizer or PCR techniques. Once obtained, sequences encoding the immunoglobulins are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence.

In general, plasmid vectors containing replicon and control sequences which are derived from a species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In some embodiments, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

Prokaryotic host cells suitable for expressing polypeptides include Archaebacteria and Eubacteria, such as Gram-negative or Gram-positive organisms. Examples of useful bacteria include *Escherichia* (e.g., *E. coli*), *Bacilli* (e.g., *B. subtilis*),

*Enterobacteria, Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. Preferably the host cell should secrete minimal amounts of proteolytic enzymes, and additional protease inhibitors may desirably be incorporated in the cell culture.

Peptide/Polypeptide Production

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the peptides/polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

Peptide/polypeptides described herein expressed in a microorganism may be secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therefrom. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

Besides prokaryotic host cells, eukaryotic host cell systems are also well established in the art. Suitable hosts include mammalian cell lines such as CHO, and insect cells such as those described below.

Peptide/Polypeptide Purification

Peptides/polypeptides that are produced may be purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

METHODS OF THE INVENTION

The invention provides various methods based on the finding that mutations in certain regions of the HGF β chain result in modification of the biological activities of the molecule, whereby such mutant molecules exhibit antagonistic effects in the modulation of the HGF/Met pathway.

Various substances or molecules (including peptides/polypeptides, etc.) may be employed as therapeutic agents in accordance with the methods of the invention. These substances or molecules can be formulated according to known methods to prepare pharmaceutically useful compositions, whereby the product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a substance or molecule of the invention is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a substance or molecule is desired in a formulation with release characteristics suitable for the treatment of any disease or disorder requiring administration of the substance or molecule, microencapsulation of the substance or molecule is contemplated. Microencapsulation of recombinant proteins for sustained release has been successfully performed with human growth hormone (rhGH), interferon-(rhIFN—), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

The identification of regions within the HGF β chain that are critical for HGF function in the HGF/Met signaling pathway provides sites within HGF β chain against which antagonists can be targeted. Examples of potential antagonists include an oligonucleotide (which may be an aptamer) that binds to N-terminal and/or dimerization regions of HGF β chain, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Aptamers are nucleic acid molecules that are capable of binding to a target molecule. The generation and therapeutic use of aptamers are well established in the art. See, e.g., U.S. Pat. No. 5,475,096, and the therapeutic efficacy of Macugen® (Eyetech, New York) for treating age-related macular degeneration.

As described herein, an HGF/Met antagonist substance/molecule of the invention can be a peptide or polypeptide (including an antibody). Methods of obtaining such peptides and polypeptides are well known in the art, and include screening peptide and polypeptide libraries for binders to a suitable target antigen. In one embodiment, suitable target antigens would comprise HGF β chain (or portion thereof that comprises the N-terminal and/or dimerization region), which is described in detail herein. In one embodiment, suitable target antigens would comprise Met, for example the extracellular domain of Met. Libraries of peptides and polypeptides are well known in the art, and can also be prepared according to art methods. See, e.g., Clark et al., U.S. Pat. Nos. 6,121,416; and Garrard et al., U.S. Pat. Nos. 5,750,373, 5,733,743, 5,837,242, 5,969,108, 6,172,197, 5,580,717, and 5,658,727. Libraries of peptides and polypeptides fused to a heterologous protein component, such as a phage coat protein, are well known in the art, e.g., as described in Clark et al. and Garrard et al., supra. Variants of a first selected peptide or polypeptide binder can be generated by screening mutants of the peptide or polypeptide to obtain the characteristics of interest (e.g., enhancing target binding affinity, enhanced pharmacokinetics, reduced toxicity, improved therapeutic index, etc.). For example a characteristic of interest can be ability to bind to Met, but reduced ability to activate HGF-related biological activities such as cell proliferation, Met phosphorylation, cell migration, and angiogenesis. Mutagenesis techniques are well known in the art, and regions for mutation would be within the HGF β chain, in particular positions associated with HGF β chain N-terminus insertion and/or β chain-β chain dimerization as described herein. Furthermore, scanning mutagenesis techniques (such as those based on alanine scanning) can be especially helpful to assess structural and/or functional importance of individual amino acid residues within a peptide or polypeptide.

Determination of the ability of a candidate substance/molecule of the invention to modulate HGF/c-met signaling and/or biological activities associated with said signaling can be performed by testing the modulatory capability of the substance/molecule in in vitro or in vivo assays, which are well established in the art, e.g., as described in Okigaki et al., supra; Matsumoto et al., supra; Date et al., FEBS Let. (1997), 420:1-6; Lokker et al., supra; Hartmann et al., supra; Kirchhofer et al., J Biol. Chem. (2004), 279:39915-24; Stamos et al. (2004) EMBO J. 23: 2325-35; Kirchhofer et al., FEBS Lett. (2005) 579: 1945-50; and Nakatsu et al. (Microvasc. Res. 66: 102, 2003).

HGF β Chain Antibodies

The present invention further provides methods comprising use of antibodies. Exemplary antibodies include polyclonal, monoclonal, humanized, bispecific, and heteroconjugate antibodies.

1. Polyclonal Antibodies

The antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include an HGF β chain (or portion thereof) or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the HGF β chain (or portion thereof) or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51-63].

The culture medium in which the hybridoma cells are cultured can then be assayed for the presence of monoclonal antibodies directed against HGF β chain. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Antibodies can also be generated by screening phage display libraries for antibodies or antibody fragments that bind with suitable/desired affinity to HGF β chain (or equivalent).

Such techniques are well known in the art, for e.g., as disclosed in U.S. Pat. Nos. 5,750,373; 5,780,279; 5,821,047; 6,040,136; 5,427,908; 5,580,717, and references therein.

3. Human and Humanized Antibodies

The HGF β chain antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for HGF β chain, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on HGF β chain or to an epitope on HGF β chain and an epitope on another polypeptide (e.g., c-met or HGF α chain).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

9. Pharmaceutical Compositions of Antibodies

Antibodies can be administered for the treatment of various disorders in the form of pharmaceutical compositions.

If whole antibodies are used as inhibitors, internalizing antibodies are preferred. However, lipofections or liposomes can also be used to deliver antibodies of the invention into cells where that is desired. Where antibody fragments are used, the smallest inhibitory fragment is preferred. For example, based upon the variable-region sequences of an antibody, peptide and polypeptide molecules can be designed that retain the ability to bind HGF β chain and/or interfere with interaction between HGF β chain and c-met, interfere with insertion of HGF β chain N-terminus, and/or interfere with HGF β chain-β chain interaction. Such peptides and polypeptides can be synthesized chemically and/or produced by recombinant DNA technology. See, e.g., Marasco et al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919) copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The following are examples of the methods and compositions of the invention. It is understood that various other embodiments may be practiced, given the general description provided above.

EXAMPLES

Materials & Methods

HGF mutants were generated essentially as described in Kirchhofer et al., J Biol. Chem. (2004), 279:39915-24; Stamos et al. (2004) EMBO J. 23: 2325-35. Met binding and MDA-MB435 cell migration assays were performed using reagents and methods as described in Kirchhofer et al., supra. and Stamos et al., supra. Met phosphorylation assays were carried out using A549 cells essentially as described in Kirchhofer et al., supra. Inhibition of Met phosphorylation was carried out similarly except that HGF mutants were added in a dose dependent manner to inhibit phosphorylation using 50 ng/ml HGF. Inhibition of cell proliferation was carried out in BxPC3 assays essentially as described in Kirchhofer et al., FEBS Lett. (2005) 579: 1945-50. In-vitro angiogenesis assay was carried out essentially as described by Nakatsu et al. (Microvasc. Res. 66: 102, 2003). The HGF mutants were added to the culture medium at a concentration of 10 μg/ml every other day during a 6-day experiment. At the end of the experiment the number of sprouts per bead was quantified and expressed as the average±SD of 4 independent experiments.

Results

Figure 2B:
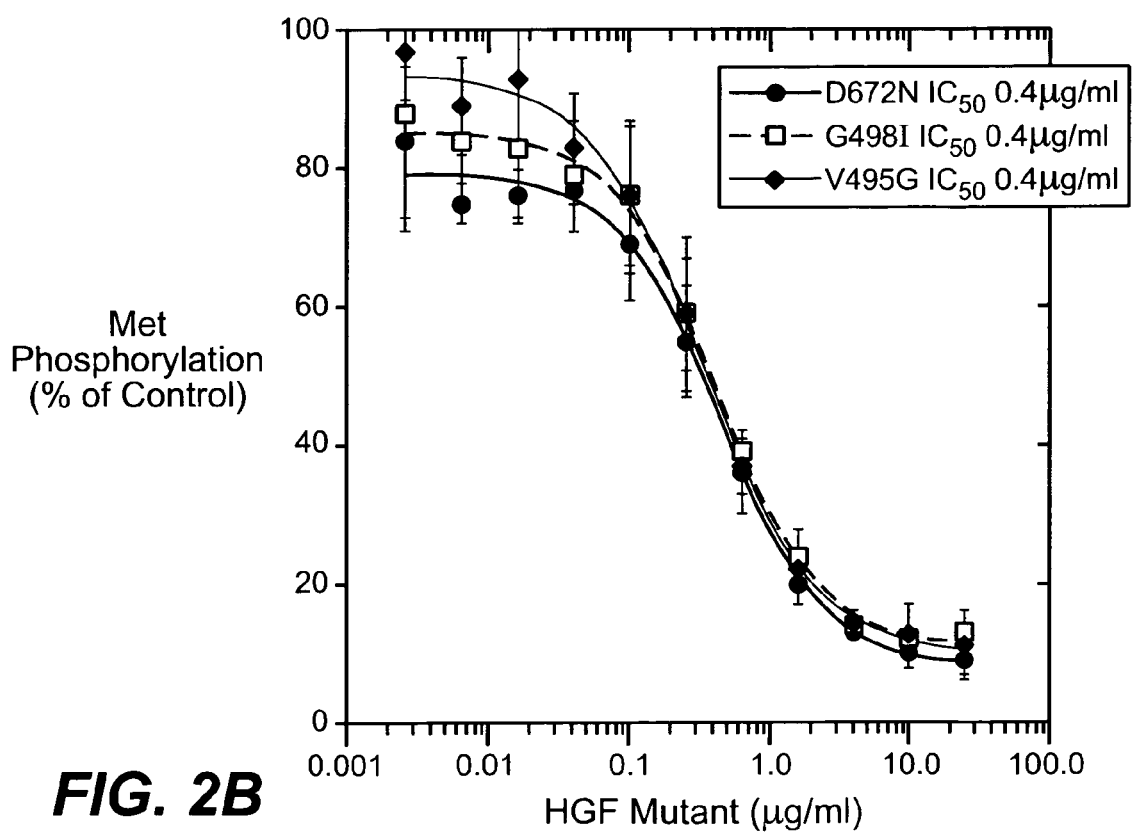
Figure 3B:
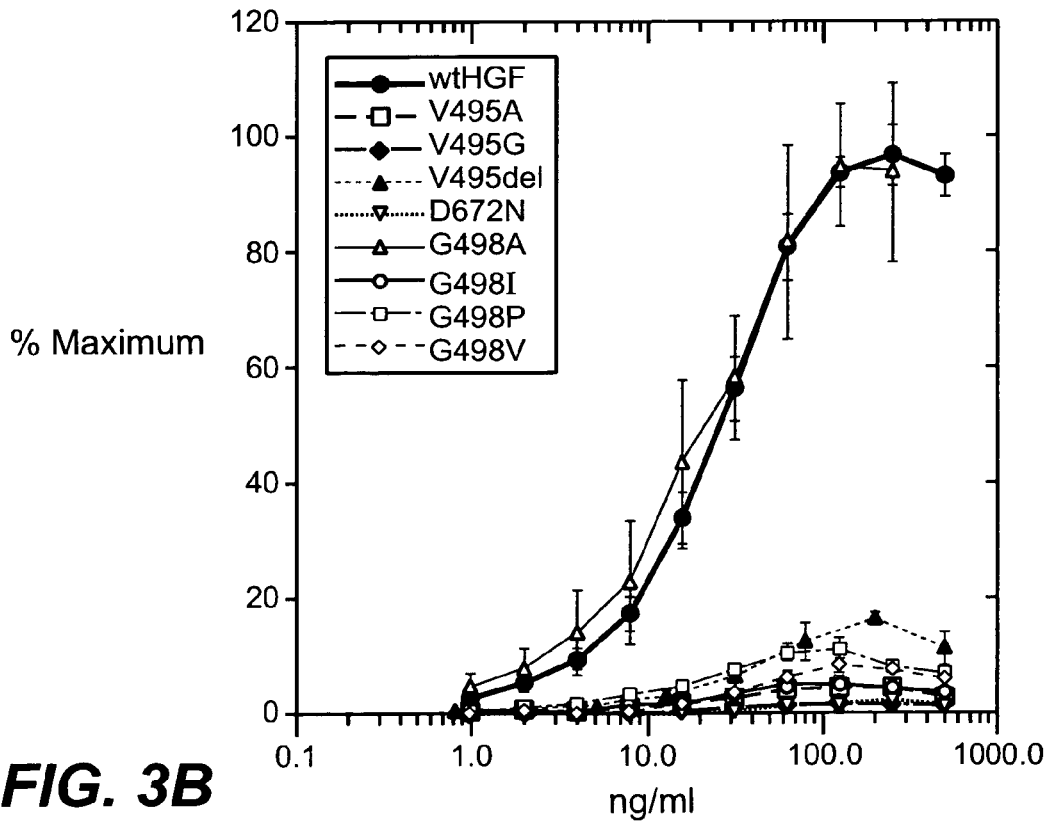

HGF β chain mutants (as β chain alone and as full-length HGF), having the mutations as indicated, were characterized for ability to bind MetIgG, in comparison to wild type HGF β chain (β chain alone and full-length HGF) using a competition ELISA assay. In order to minimize any potential disulfide-linked dimer formation, wild type HGF β and HGF β chain mutants were made in the C604S background; thus wild type HGF β is actually HGF β C604S. In addition, selected full-length 2-chain HGF mutants were assessed in a cell migration assay to determine effects, if any, on biological function, as a result of the mutations in the β chain. Results are depicted in FIGS. 1A, B, C. HGF mutant G498I inhibited HGF-dependent phosphorylation of Met in a dose dependent manner as depicted in FIG. 2; results for HGF mutant R424A: R494E (single-chain HGF) are also shown. HGF mutants G498I and G498P activate Met significantly less well compared to wild type HGF in the Met phosphorylation assay as depicted in FIG. 3; results for HGF mutant R424A:R494E are also shown. HGF-dependent phosphorylation of Met was modulated in a dose dependent manner. Mutants HGF G498I and G498P also inhibited BxPC3 cell proliferation, having 2.5% and 56% of the activity of wild type HGF. Furthermore, selected full-length HGF mutants at a concentration of 10 µg/ml (D672N, V495G, G498I, R424A:R494E) inhibited angiogenesis in an in-vitro assay (FIG. 4), thus further confirming the significance of the HGF β chain (and selected mutations thereof) to the overall biological function of HGF.

PARTIAL LIST OF REFERENCES

Angeloni, D., Danilkovitch-Miagkova, A., Miagkov, A., Leonard, E. J., and Lerman, M. I. (2004). The soluble sema domain of the RON receptor inhibits MSP-induced receptor activation. J. Biol. Chem., 279, 3726-3732.

Birchmeier, C., Birchmeier, W., Gherardi, E., and Vande Woude, G. F. (2003). Met, metastasis, motility and more. Nature Rev. Mol. Cell Biol. 4, 915-925.

Boose, J. A., Kuismanen, E., Gerard, R., Sambrook, J., and Gething, M. J. (1989). The single-chain form of tissue-type plasminogen activator has catalytic activity: Studies with a mutant enzyme that lacks the cleavage site. Biochemistry 28, 638-643.

Bottaro, D. P., Rubin, J. S., Faletto, D. L., Chan, A. M., Kmiecik, T. E., Vande Woude, G. F., and Aaronson, S. A. (1991). Identification of the hepatocyte growth factor receptor as the c-met proto-oncogene product. Science 251, 802-804.

Broze Jr., G. J. (2001). Protein Z-dependent regulation of coagulation. Thromb. Haemost. 86, 8-13.

CCP4 (1994). The CCP4 suite: Programs for protein crystallography. Acta Crystallogr D50, 760-763.

Chirgadze et al., FEBS Letters (1998), 430:126-129.

Cohen, G. H. (1997). Align—a program to superimpose protein coordinates, accounting for insertions and deletions. J Appl. Crystallog. 30, 1160-1161.

Cooper, C. S., Blair, D. G., Oskarsson, M. K., Tainsky, M. A., Eader, L. A., and Vande Woude, G. F. (1984a). Characterization of human transforming genes from chemically transformed, teratocarcinoma, and pancreatic carcinoma cell lines. Cancer Res. 44, 1-10.

Cooper, C. S., Park, M., Blair, D. G., Tainsky, M. A., Huebner, K., Croce, C. M., and Vande Woude, G. F. (1984b). Molecular cloning of a new transforming gene from a chemically transformed human cell line. Nature 311, 29-33.

Danilkovitch, A., Miller, M., and Leonard, E. J. (1999). Interaction of macrophage-stimulating protein with its receptor. J. Biol. Chem. 274, 29937-29943.

Danilkovitch-Miagkova, A., and Zbar, B. (2002). Dysregulation of Met receptor tyrosine kinase activity in invasive tumors. J. Clin. Invest. 109, 863-867.

Date et al., FEBS Lett. (1997), 420:1-6.

Dennis, M. S., Eigenbrot, C., Skelton, N. J., Ultsch, M. H., Santell, L., Dwyer, M. A., O'Connell, M. P., and Lazarus, R. A. (2000). Peptide exosite inhibitors of factor VIIa as anticoagulants. Nature 404, 465-470.

Derksen, P. W., Keehnen, R. M. J., Evers, L. M., van Oers, M. H. J., Spaargaren, M., and Pals, S. T. (2002). Cell surface proteoglycan syndecan-1 mediates hepatocyte growth factor binding and promotes Met signalling in multiple myeloma. Blood 99, 1405-1410.

Di Cera, E., Guinto, E. R., Vindigni, A., Dang, Q. D., Ayala, Y. M., Wuyi, M., and Tulinsky, A. (1995). The Na$^+$ binding site of thrombin. J. Biol. Chem. 270, 22089-22092.

Dickinson, C. D., Kelly, C. R., and Ruf, W. (1996). Identification of surface residues mediating tissue factor binding and catalytic function of the serine protease factor VIIa. Proc. Natl. Acad. Sci. USA 93, 14379-14384.

Donate, L. E., Gherardi, E., Srinivasan, N., Sowdhamini, R., Aparicio, S., and Blundell, T. L. (1994). Molecular evolution and domain structure of plasminogen-related growth factors (HGF/SF and HGF1/MSP). Protein Sci. 3, 2378-2394.

Drain, J., Bishop, J. R., and Hajduk, S. L. (2001). Haptoglobin-related protein mediates trypanosome lytic factor binding to Trypanosomes. J. Biol. Chem. 276, 30254-30260.

Gherardi, E., Youles, M. E., Miguel, R. N., Blundell, T. L., Iamele, L., Gough, J., Bandyopadhyay, A., Hartmann, G., and Butler, P. J. (2003). Functional map and domain structure of MET, the product of the c-met protooncogene and receptor for hepatocyte growth factor/scatter factor. Proc. Natl. Acad. Sci. USA 100, 12039-12044.

Hartmann, G., Naldini, L., Weidner, K. M., Sachs, M., Vigna, E., Comoglio, P. M., and Birchmeier, W. (1992). A functional domain in the heavy chain of scatter factor/hepatocyte growth factor binds the c-Met receptor and induces cell dissociation. Proc. Natl. Acad. Sci. USA 89, 11574-11578.

Hartmann, G., Prospero, T., Brinkmann, V., Ozcelik, C., Winter, G., Hepple, J., Batley, S., Bladt, F., Sachs, M., Birchmeier, C., et al. (1998). Engineered mutants of HGF/SF with reduced binding to heparan sulphate proteoglycans, decreased clearance and enhanced activity in vivo. Curr. Biol. 8, 125-134.

Hedstrom, L. (2002). Serine protease mechanism and specificity. Chem. Rev. 102, 4501-4523.

Huber, R., and Bode, W. (1978). Structural basis of the activation and action of trypsin. Acc Chem. Res. 11, 114-122.

Kunkel, T. A. (1985) Proc. Natl. Acad. Sci USA 82, 488-492.

Kurosky, A., Barnett, D. R., Lee, T. H., Touchstone, B., Hay, R. E., Arnott, M. S., Bowman, B. H., and Fitch, W. M. (1980). Covalent structure of human haptoglobin: a serine protease homolog. Proc. Natl. Acad. Sci. USA 77, 3388-3392.

Lijnen, H. R., Van Hoef, B., Nelles, L., and Collen, D. (1990). Plasminogen activation with single-chain urokinase-type plasminogen activator (scu-PA). Studies with active site mutagenized plasminogen (Ser$^{740}$→Ala) and plasmin-resistant scu-PA (Lys$^{158}$→Glu). J. Biol. Chem. 265, 5232-5236.

Lin, C.-Y., Anders, J., Johnson, M., Sang, Q. A., and Dickson, R. B. (1999). Molecular cloning of cDNA for matriptase, a matrix-degrading serine protease with trypsin-like activity. J. Biol. Chem. 274, 18231-18236.

Lokker, N. A., Mark, M. R., Luis, E. A., Bennett, G. L., Robbins, K. A., Baker, J. B., and Godowski, P. J. (1992). Structure-function analysis of hepatocyte growth factor: identification of variants that lack mitogenic activity yet retain high affinity receptor binding. EMBO J. 11, 2503-2510.

Lokker, N. A., Presta, L. G., and Godowski, P. J. (1994). Mutational analysis and molecular modeling of the N-terminal kringle-containing domain of hepatocyte growth factor identifies amino acid side chains important for interaction with the c-Met receptor. Protein Eng. 7, 895-903.

Ma, P. C., Maulik, G., Christensen, J., and Salgia, R. (2003). c-Met: structure, functions and potential for therapeutic inhibition. Cancer Metastasis Rev. 22, 309-325.

Malkowski, M. G., Martin, P. D., Guzik, J. C., and Edwards, B. F. P. (1997). The co-crystal structure of unliganded bovine α-thrombin and prethrombin-2: movement of the Tyr-Pro-Pro-Trp segment and active site residues upon ligand binding. Protein Sci. 6, 1438-1448.

Mark, M. R., Lokker, N. A., Zioncheck, T. F., Luis, E. A., and Godowski, P. J. (1992). Expression and characterization of hepatocyte growth factor receptor-IgG fusion proteins. Effects of mutations in the potential proteolytic cleavage site on processing and ligand binding. J. Biol. Chem. 267, 26166-26171.

Matsumoto, K., Takehara, T., Inoue, H., Hagiya, M., Shimizu, S., and Nakamura, T. (1991). Biochem. Biophys. Res. Commun. 181, 691-699.

Matsumoto, K., Kataoka, H., Date, K., and Nakamura, T. (1998). Cooperative interaction between α- and β-chains of hepatocyte growth factor on c-Met receptor confers ligand-induced receptor tyrosine phosphorylation and multiple biological responses. J. Biol. Chem. 273, 22913-22920.

Maulik, G., Shrikhande, A., Kijima, T., Ma, P. C., Morrison, P. T., and Salgia, R. (2002). Role of the hepatocyte growth factor receptor, c-Met, in oncogenesis and potential for therapeutic inhibition. Cytokine Growth Factor Rev. 13, 41-59.

Miller, M., and Leonard, E. J. (1998). Mode of receptor binding and activation by plasminogen-related growth factors. FEBS Lett. 429, 1-3.

Miyazawa, K., Shimomura, T., Kitamura, A., Kondo, J., Morimoto, Y., and Kitamura, N. (1993). Molecular cloning and sequence analysis of the cDNA for a human serine protease responsible for activation of hepatocyte growth factor. J. Biol. Chem. 268, 10024-10028.

Naka, D., Ishii, T., Yoshiyama, Y., Miyazawa, K., Hara, H., Hishida, T., and Kitamura, N. (1992). Activation of hepatocyte growth factor by proteolytic conversion of single chain form to a heterodimer. J. Biol. Chem. 267, 20114-20119.

Nakamura, T., Nishizawa, T., Hagiya, M., Seki, T., Shimonishi, M., Sugimura, A., Tashiro, K., and Shimizu, S. (1989). Molecular cloning and expression of human hepatocyte growth factor. Nature 342, 440-443.

Naldini, L., Tamagnone, L., Vigna, E., Sachs, M., Hartmann, G., Birchmeier, W., Daikuhara, Y., Tsubouchi, H., Blasi, F., and Comoglio, P. M. (1992). Extracellular proteolytic cleavage by urokinase is required for activation of hepatocyte growth factor/scatter factor. EMBO J. 11, 4825-4833.

Okigaki, M., Komada, M., Uehara, Y., Miyazawa, K., and Kitamura, N. (1992). Functional characterization of human hepatocyte growth factor mutants obtained by deletion of structural domains. Biochemistry 31, 9555-9561.

Parry, M. A., Fernandez-Catalan, C., Bergner, A., Huber, R., Hopfner, K. P., Schlott, B., Guhrs, K. H., and Bode, W. (1998). The ternary microplasmin-staphylokinase-microplasmin complex is a proteinase-cofactor-substrate complex in action. Nat. Struct. Biol. 5, 917-923.

Peek, M., Moran, P., Mendoza, N., Wickramasinghe, D., and Kirchhofer, D. (2002). Unusual proteolytic activation of pro-hepatocyte growth factor by plasma kallikrein and coagulation factor XIa. J. Biol. Chem. 277, 47804-47809.

Peisach, E., Wang, J., de los Santos, T.; Reich, E., and Ringe, D. (1999). Crystal structure of the proenzyme domain of plasminogen. Biochemistry 38, 11180-11188.

Perona, J. J., and Craik, C. S. (1995). Structural basis of substrate specificity in the serine proteases. Protein Sci. 4, 337-360.

Rawlings, N. D., O'Brien, E., and Barrett, A. J. (2002). MEROPS: the protease database. Nucl. Acid Res. 30, 343-346.

Renatus, M., Engh, R. A., Stubbs, M. T., Huber, R., Fischer, S., Kohnert, U., and W., B. (1997). Lysine 156 promotes the anomalous proenzyme activity of tPA: X-ray crystal structure of single-chain human tPA. EMBO J. 16, 4797-4805.

Richardson, J. L., Kroger, B., Hoeffken, W., Sadler, J. E., Pereira, P., Huber, R., Bode, W., and Fuentes-Prior, P. (2000). Crystal structure of the human α-thrombin-haemadin complex: an exosite II-binding inhibitor. EMBO J. 19, 5650-5660.

Shimomura, T., Miyazawa, K., Komiyama, Y., Hiraoka, H., Naka, D., Morimoto, Y., and Kitamura, N. (1995). Activation of hepatocyte growth factor by two homologous proteases, blood-coagulation factor XIIa and hepatocyte growth factor activator. Eur J Biochem 229, 257-261.

Stubbs, M., and Bode, W. (1993). A player of many parts: The spotlight falls on thrombin's structure. Thromb. Res. 69, 1-58.

Takeuchi, T., Shuman, M. A., and Craik, C. S. (1999). Reverse biochemistry: use of macromolecular protease inhibitors to dissect complex biological processes and identify a membrane-type serine protease in epithelial cancer and normal tissue. Proc Natl Acad Sci USA 96, 11054-11061.

Trusolino et al., FASEB J. (1998), 12:1267-1280.

Trusolino, L., and Comoglio, P. M. (2002). Scatter-factor and semaphorin receptors: cell signalling for invasive growth. Nature Rev. Cancer 2, 289-300.

Tsiang, M., Jain, A. K., Dunn, K. E., Rojas, M. E., Leung, L. L. K., and Gibbs, C. S. (1995). Functional mapping of the surface residues of human thombin. J. Biol. Chem. 270, 16854-16863.

Vijayalakshmi, J., Padmanabhan, K. P., Mann, K. G., and Tulinsky, A. (1994). The isomorphous structures of prethrombin2, hirugen-, and PPACK-thrombin: changes accompanying activation and exosite binding to thrombin. Protein Sci. 3, 2254-2271.

Wang, D., Bode, W., and Huber. R (1985). Bovine chymotrypsinogen A: x-ray crystal structure analysis and refinement of a new crystal form at 1.8 Å resolution. J. Mol. Biol. 185, 595-624.

Wang, D., Julian, F. M., Breathnach, R., Godowski, P. J., Takehara, T., Yoshikawa, W., Hagiya, M., and Leonard, E. J. (1997). Macrophage stimulating protein (MSP) binds to its receptor via the MSP β chain. J. Biol. Chem. 272, 16999-17004.

The invention claimed is:

1. A method of inhibiting c-met activation in a subject, said method comprising administering to the subject an HGF/c-met antagonist molecule, whereby c-met activation is inhibited, wherein the HGF/c-met antagonist molecule comprises an HGF mutant comprising a mutation in HGF β chain N terminal region, wherein the mutation in HGF β chain N terminal region is G498I, G498P, G498V, R502del plus T503del, or D672N.

2. A method of inhibiting c-met activation in a subject, said method comprising administering to the subject an HGF/c-met antagonist molecule, whereby c-met activation is inhibited, wherein the HGF/c-met antagonist molecule comprises an HGF mutant comprising a mutation in HGF β chain dimerization region, wherein the mutation in HGF β chain dimerization region is N497R or K, G498A or S, P500W, H or E, or R502del.

3. The method of claim 1 or 2, wherein c-met modulated cell proliferation, cell migration and angiogenic activity is inhibited.

4. The method of claim 1 or 2, wherein the molecule comprises wild type amino acids at positions 534, 578, 619, 673, 692, 693, 694, 695, 696, 699 and/or 702.

5. The method of claim 1, wherein the mutation in HGF β chain N terminal region is G498I.

6. The method of claim 1, wherein the mutation in HGF β chain N terminal region is G498P.

7. The method of claim 1, wherein the mutation in HGF β chain N terminal region is G498V.

8. The method of claim 1, wherein the mutation in HUF β chain N terminal region is R502del plus T503del.

9. The method of claim 1, wherein the mutation in HGF β chain N terminal region is D672N.

10. The method of claim 2, wherein the mutation in HGF β chain dimerization region is N497R.

11. The method of claim 2, wherein the mutation in HGF β chain dimerization region is N497K.

12. The method of claim 2, wherein the mutation in HGF β chain dimerization region is G498A.

13. The method of claim 2, wherein the mutation in HGF β chain dimerization region is G498S.

14. The method of claim 2, wherein the mutation in HGF β chain dimerization region is P500W.

15. The method of claim 2, wherein the mutation in HGF β chain dimerization region is P500H.

16. The method of claim 2, wherein the mutation in HGF β chain dimerization region is P500E.

17. The method of claim 2, wherein the mutation in HGF β chain dimerization region is R502del.

* * * * *

UNITED STATES PATENT AND TRADEMARK OFFICE
CERTIFICATE OF CORRECTION

PATENT NO.       : 7,737,115 B2
APPLICATION NO.  : 11/406067
DATED            : June 15, 2010
INVENTOR(S)      : Kirchhofer et al.

It is certified that error appears in the above-identified patent and that said Letters Patent is hereby corrected as shown below:

On the Title Page, Item (73): please replace "Genetech" with -- Genentech --

Signed and Sealed this

Sixteenth Day of November, 2010

David J. Kappos
*Director of the United States Patent and Trademark Office*